(12) United States Patent
Saroha et al.

(10) Patent No.: US 11,464,481 B2
(45) Date of Patent: Oct. 11, 2022

(54) CONTROL HANDLE FOR STEERABLE MEDICAL DEVICES

(71) Applicant: PHILIPS IMAGE GUIDED THERAPY CORPORATION, San Diego, CA (US)

(72) Inventors: Princeton Saroha, Ladera Ranch, CA (US); Norman H. Hossack, Ladera Ranch, CA (US); Jeremy Stigall, San Diego, CA (US); Maritess Minas, Eindhoven (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 545 days.

(21) Appl. No.: 16/336,524

(22) PCT Filed: Sep. 29, 2017

(86) PCT No.: PCT/EP2017/074753
§ 371 (c)(1),
(2) Date: Mar. 26, 2019

(87) PCT Pub. No.: WO2018/060411
PCT Pub. Date: Apr. 5, 2018

(65) Prior Publication Data
US 2021/0298718 A1 Sep. 30, 2021

Related U.S. Application Data

(60) Provisional application No. 62/434,093, filed on Dec. 14, 2016, provisional application No. 62/402,483, filed on Sep. 30, 2016.

(51) Int. Cl.
*A61B 8/12* (2006.01)
*A61B 8/00* (2006.01)

(52) U.S. Cl.
CPC .............. *A61B 8/12* (2013.01); *A61B 8/42* (2013.01); *A61B 8/4455* (2013.01)

(58) Field of Classification Search
CPC ......... A61B 1/00066; A61B 8/12; A61B 8/42; A61B 8/4455; A61B 8/4466
See application file for complete search history.

(56) References Cited

U.S. PATENT DOCUMENTS 5,671,748 A * 9/1997 Itoi .................... A61B 1/00165
600/117
6,210,337 B1 * 4/2001 Dunham .............. A61B 1/0052
600/462

(Continued)

FOREIGN PATENT DOCUMENTS

| EP | 2428169 A1 | 3/2012 |
| JP | 2009056316 A | 3/2009 |
| WO | 2007115307 A2 | 10/2007 |

*Primary Examiner* — Oommen Jacob
*Assistant Examiner* — Maria Christina Talty

(57) ABSTRACT

An intraluminal imaging device includes a flexible elongate shaft including a distal portion and a proximal portion, wherein the flexible elongate shaft is configured for insertion into a patient body; a distal tip that comprises an imaging element and is operably associated with the distal portion of the flexible elongate shaft; and a control handle coupled to the proximal portion of the flexible elongate shaft, wherein the control handle includes: a first actuator configured to position the imaging element within the patient body; and a first frictional member coupled to the first actuator and arranged to contact the first actuator to control positioning of the imaging element. Associated devices, systems, and methods are also provided.

30 Claims, 18 Drawing Sheets

(56) References Cited

U.S. PATENT DOCUMENTS

| | | | | |
|---|---|---|---|---|
| 2009/0287188 A1* | 11/2009 | Golden | ............ | A61M 25/0147 |
| | | | | 604/528 |
| 2009/0318003 A1* | 12/2009 | Hossack | ................ | A61B 8/445 |
| | | | | 439/299 |
| 2012/0053417 A1* | 3/2012 | Yamakawa | .......... | A61B 1/0016 |
| | | | | 600/144 |
| 2013/0047757 A1* | 2/2013 | Okamoto | ........... | A61B 1/00066 |
| | | | | 74/89.22 |
| 2013/0131592 A1* | 5/2013 | Selkee | .............. | A61M 25/0136 |
| | | | | 604/95.04 |
| 2013/0184691 A1* | 7/2013 | Oskin | ................. | A61B 1/0014 |
| | | | | 606/1 |
| 2013/0204096 A1* | 8/2013 | Ku | ....................... | A61B 1/0058 |
| | | | | 600/301 |
| 2015/0057610 A1 | 2/2015 | Osypka et al. | | |

\* cited by examiner

CONTROL HANDLE FOR STEERABLE MEDICAL DEVICES

RELATED APPLICATIONS

This application is the U.S. National Phase application under 35 U.S.C. § 371 of International Application No. PCT/EP2017/074753, filed on Sep. 29, 2017, which claims the benefit of and priority to U.S. Provisional Application Ser. No. 62/402,483, filed Sep. 30, 2016 and 62/434,093, filed Dec. 14, 2016, which are incorporated by reference in their entireties.

TECHNICAL FIELD

The present disclosure relates generally to ultrasound catheters, in particular, to a steerable intracardiac echocardiography (ICE) catheter having an ergonomic control handle with a variable braking system to provide intuitive and fine steering control of the catheter.

BACKGROUND

Diagnostic and therapeutic ultrasound catheters have been designed for use inside many areas of the human body. In the cardiovascular system, two common diagnostic ultrasound methods are intravascular ultrasound (IVUS) and intracardiac echocardiography (ICE). Typically a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

IVUS catheters are typically used in the large and small blood vessels (arteries or veins) of the body, and are almost always delivered over a guidewire having a flexible tip. ICE catheters are usually used to image chambers of the heart and surrounding structures, for example, to guide and facilitate medical procedures, such as transseptal lumen punctures, left atrial appendage closures, atrial fibrillation ablation, and valve repairs. Commercially-available ICE catheters are not designed to be delivered over a guidewire, but instead have distal ends which can be articulated by a steering mechanism located in a handle at the proximal end of the catheter. For example, an ICE catheter may be inserted through the femoral or jugular artery when accessing the anatomy, and steered in the heart to acquire images necessary to the safety of the medical procedures.

One type of ICE catheter (EP Medsystems ViewFlex™ Intracardiac Ultrasound Deflectable catheter) has a distal articulation in a single plane (both directions), operated by a single wheel that rotates about the lengthwise axis of the handle. The wheel is turned to a specific position for the desired catheter shape, staying in place due to the inherent friction on the wheel mechanism. The catheter is torquable, and can be rotated with the handle to facilitate steering in a second plane. The motions required to simultaneously torque and rotate the catheter often require two-handed operation.

Another type of ICE catheter (Siemens/ACUSON Acu-Nav™ Ultrasound Catheter) has an additional steering plane, and each steering plane is utilized by turning one of two corresponding wheels on the handle. These wheels rotate about the lengthwise axis of the handle. A third wheel, which also rotates about the lengthwise axis of the handle, is a locking mechanism for freezing each of the two steering wheels in its respective orientation. The entire catheter need not be torqued. The two steering planes allow a large combination of possible catheter configurations. However, simultaneous steering of both planes to achieve a desired articulation view may be difficult to visualize and coordinate.

SUMMARY

While existing ICE catheter devices have proved useful, there remains a need for improved systems and techniques for providing fine and intuitive steering controls of the catheter devices. Embodiments of the present disclosure provide a catheter including steering system and brake system that controls how the distal end of the catheter is deflected. The distal end of the catheter, including an imaging element, can be selectively deflected by a user, such a physician in order to obtain a better view of anatomy to be imaged. A steering mechanism, including one or more rotatable wheels, deflects the catheter in one or more direction. When the user wants to maintain the catheter in the deflected position, a braking mechanism either slow the cathether's return to being straight and un-deflected or the lock the catheter in the deflected position. The braking mechanism can be adjusted so that the rate at which the cathether return's to being straight and un-deflected can be change by the user.

In one embodiment, an intraluminal imaging device is provided. The intraluminal imaging device includes a flexible elongate shaft including a distal portion and a proximal portion, wherein the flexible elongate shaft is configured for insertion into a patient body; a distal tip that comprises an imaging element and is operably associated with the distal portion of the flexible elongate shaft; and a control handle coupled to the proximal portion of the flexible elongate shaft, wherein the control handle includes: a first actuator configured to position the imaging element within the patient body; and a first frictional member coupled to the first actuator and arranged to contact the first actuator to control positioning of the imaging element.

In some embodiments, the first actuator includes: a first pulley member coupled to a first pair of pullwire segments, wherein the first pair of pullwire segments are coupled to the distal portion of the flexible elongate shaft; and a first actuation control member coupled to the first pulley member and configured to apply tension to the first pair of pullwire segments such that the imaging element and the distal portion of the flexible elongate shaft are deflected along a first plane, wherein the first frictional member is positioned on a side of the first actuation control member opposite to the first pulley member. In some embodiments, an outer circumference of the first frictional member includes one or more interfering posts oriented towards a cavity of the first actuation control member; the one or more interfering posts contact the first actuation control member in response to application of a compression force on the first actuation control member; and contact between the interfering posts and the first actuation control member changes rotational resistance of the first actuation control member. In some embodiments, the control handle further includes: a clutch spring coupled to the first pulley member; a clutch cam coupled to the clutch spring; and a clutch control member coupled to the clutch cam such that adjustment of the clutch control member causes the clutch cam to compress the clutch spring towards the first pulley member such that the compression force is applied to the first actuation control member. In some embodiments, the control handle further includes a housing having an elongate shape, wherein the first frictional member, the first actuator, the clutch spring, the clutch cam, and the clutch control member are disposed at a distal portion of the housing, and wherein the housing includes a plurality of finger-shaped grooves positioned on an outer surface of a proximal portion of the housing. In some embodiments, the control handle further includes: an axle extending through the clutch spring, the first pulley member, the first actuation control member, and the first frictional member, wherein the housing includes a plurality of alignment members arranged to receive the axle. In some embodiments, the first frictional member further includes a locking post positioned on a side of the first frictional member opposite to the one or more interfering posts, and wherein the first actuation control member is maintained at a current position when the locking post is locked to one of the plurality of alignment members.

In some embodiments, the first actuation control member includes a first slot and a second slot, wherein the first pulley member includes a first post received within the first slot and a second post received within the second slot, and wherein the first post and the second post have different diameters. In some embodiments, the first pulley member includes: a plurality of holes radially spaced apart on a side of the first pulley member opposite to the first post and the second post; and an anchoring member disposed on an edge of the first pulley member, wherein the first pair of pullwire segments are threaded through the plurality of holes and secured to the anchoring member. In some embodiments, the control handle further comprises: a second actuator including: a second pulley member coupled to a second pair of pullwire segments, wherein the second pair of pullwire segments are coupled to the distal portion of the flexible elongate shaft; and a second actuation control member coupled to the second pulley member and configured to apply tension to the second pair of pullwire segments such that the imaging element and the distal portion of the flexible elongate shaft are deflected along a second plane different from the first plane; a second frictional member coupled to the second actuator and arranged to contact the second actuator to control positioning of the imaging element. In some embodiments, the intraluminal imaging device further comprises: a housing having an elongate shape, wherein the first actuation control member and the second actuation control member are positioned lengthwise along the housing. In some embodiments, the housing includes a routing member configured to orient a coaxial cable coupled to the imaging element such that the coaxial cable is spaced from the first pair of pullwire segments and the second pair of pullwire segments within the housing. In some embodiments, the first actuator is aligned with a central longitudinal axis of the flexible elongate shaft, and wherein the second actuator is offset from the central longitudinal axis such that actuations of the first pair of pullwire segments and the second pair of pullwire segments are independent of each other. In some embodiments, the first plane is a left-right articulation plane, wherein the second plane is an anterior-posterior articulation plane, and wherein the first actuation control member is larger in size than the second actuation control member.

In one embodiment, an ultrasound catheter assembly is provided. The ultrasound catheter assembly includes a flexible elongate shaft including a distal portion and a proximal portion, wherein the flexible elongate shaft is configured for insertion into a patient body; an imaging sensor mounted on the distal portion of the flexible elongate shaft and in communication with a coaxial cable; and a control handle coupled to the proximal portion of the flexible elongate shaft, wherein the control handle includes: a housing having an elongate shape; an actuator disposed within the housing and coupled to a plurality of pullwire segments configured to position the imaging sensor within the patient body; and a routing member disposed within the housing and configured to direct the coaxial cable away from the plurality of pullwire segments within the housing.

In some embodiments, the actuator includes: a pulley member coupled to the plurality of pullwire segments, wherein the plurality of pullwire segments are coupled to the distal portion of the flexible elongate shaft; and an actuation control member coupled to the pulley member and configured to apply tension to the plurality of pullwire segments such that the imaging sensor and the distal portion of the flexible elongate shaft are deflected, wherein the control handle further includes a frictional member coupled to the actuator and arranged to contact the actuator to control positioning of the imaging sensor. In some embodiments, the control handle further includes: a clutch spring coupled to the pulley member; a clutch cam coupled to the clutch spring; and a clutch control member coupled to the clutch cam such that adjustment of the clutch control member causes the clutch cam to compress the clutch spring towards the pulley member such that compression force is applied to the actuation control member to vary rotational resistance of the actuation control member. In some embodiments, an outer surface of the housing includes a plurality of finger-shaped grooves. In some embodiments, the control handle further includes an axle extending through the clutch spring, the pulley member, the actuation control member, and the frictional member, wherein the housing includes a plurality of alignment members arranged to receive the axle. In some embodiments, the frictional member further includes a locking post, and wherein the actuation control member is maintained at a current position when the locking post is locked to one of the plurality of alignment members.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
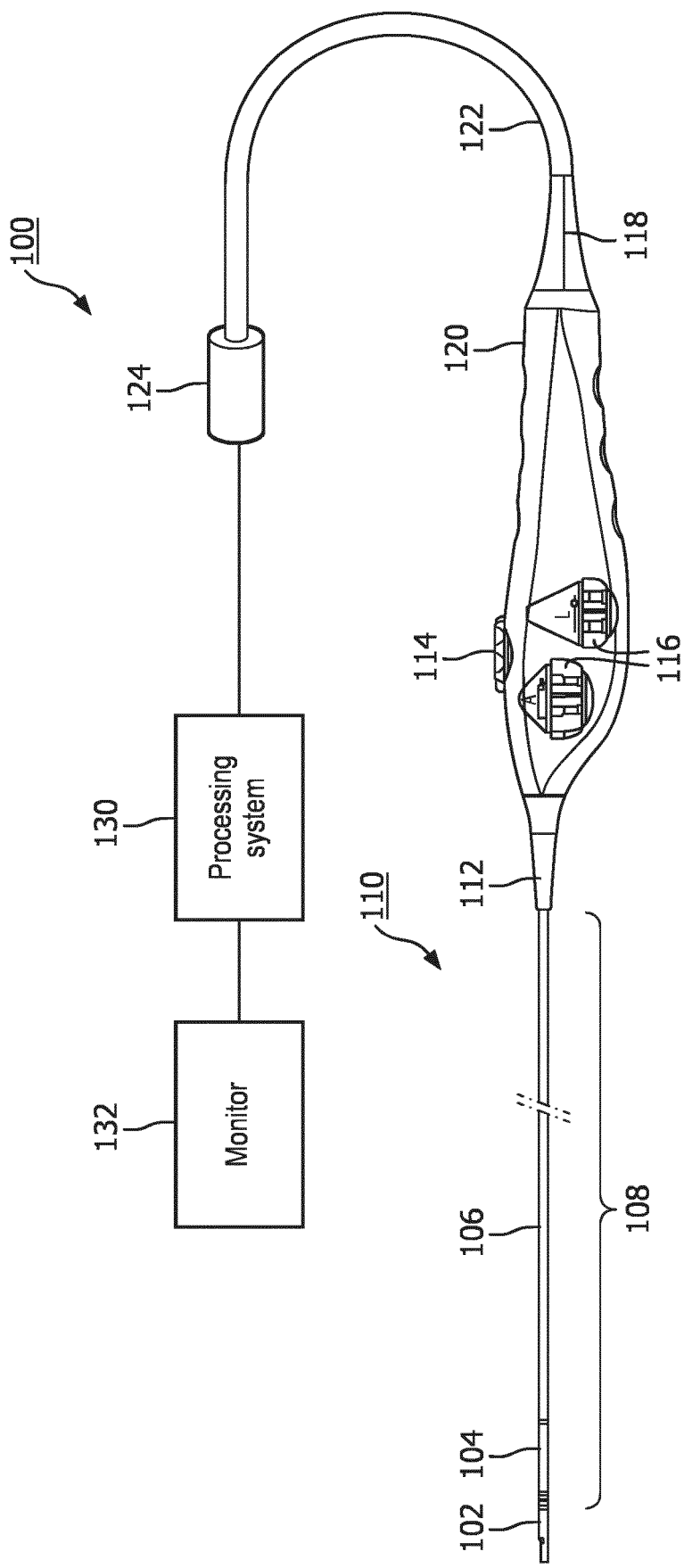
FIG. 1 is a schematic diagram of an ICE imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ICE system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ICE imaging system 100 according to embodiments of the present disclosure. The system 100 may include an ICE device 110, a connector 124, a control and processing system 130, such as a console and/or a computer, and a monitor 132. The ICE device 110 includes a tip assembly 102, a flexible elongate member 108, and a handle 120. The flexible elongate member 108 includes a distal portion 104 and a proximal portion 106. The distal end of the distal portion 104 is attached to the tip assembly 102. The proximal end of the proximal portion 106 is attached to the handle 120 for example, by a resilient strain relief 112, for manipulation of the ICE device 110 and manual control of the ICE device 110. The tip assembly 102 can include an imaging core or imaging sensor with ultrasound transducer elements and associated circuitry. The handle 120 can include actuators 116, a clutch 114, and other steering control components for steering the ICE device 110, such as deflecting the tip assembly 102 and the distal portion 104, as described in greater details herein.

The handle 120 is connected to the connector 124 via another strain relief 118 and an electrical cable 122. The connector 124 may be configured in any suitable configurations to interconnect with the processing system 130 and the monitor 132 for processing, storing, analyzing, manipulating, and displaying data obtained from signals generated by the imaging core at the tip assembly 102. The processing system 130 can include one or more processors, memory, one or more input devices, such as keyboards and any suitable command control interface device. The processing system 130 can be operable to facilitate the features of the ICE imaging system 100 described herein. For example, the processor can execute computer readable instructions stored on the non-transitory tangible computer readable medium. The monitor 132 can be any suitable display device, such as liquid-crystal display (LCD) panel or the like.

In operation, a physician or a clinician advances the flexible elongate member 108 into a vessel within a heart anatomy. Generally, the flexible elongate member 108 can be positioned within any lumen within a patient body. The ICE device 110 can be referenced as an intraluminal imaging device in some embodiments. The physician or clinician can steer the flexible elongate member 108 to a position near the area of interest to be imaged by controlling the actuators 116 and the clutch 114 on the handle 120. For example, one actuator 116 may deflect the tip assembly 102 and the distal portion 104 in a left-right plane and the other actuator 116 may deflect the tip assembly 102 and the distal portion 104 in an anterior-posterior plane, as discussed in greater details herein. The clutch 114 provides a locking mechanism to lock the positions of the actuators 116 and in turn the deflection of the flexible elongate member while imaging the area of interest.

The imaging process may include activating the ultrasound transducer elements on the tip assembly 102 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the processing system 130 where the ultrasound image is reconstructed and displayed on the monitor 132. In some embodiments, the processing system 130 can control the activation of the ultrasound transducer elements and the repletion of the echo signals. In some embodiments, the processing system 130 and the monitor 132 may be part of the same system.

The system 100 may be utilized in a variety of applications such as transseptal lumen punctures, left atrial appendage closures, atrial fibrillation ablation, and valve repairs and can be used to image vessels and structures within a living body. Although the system 100 is described in the context of ICE catheterization procedures, the system 100 is suitable for use with any catheterization procedure. In addition, the tip assembly 102 may include any suitable physiological sensor, component, and/or functional element for diagnosis, treatment, and/or therapy. Thus, the handle 120 can be used to guide articulation of any functional element at the distal end of the device 110.

Figure 2:
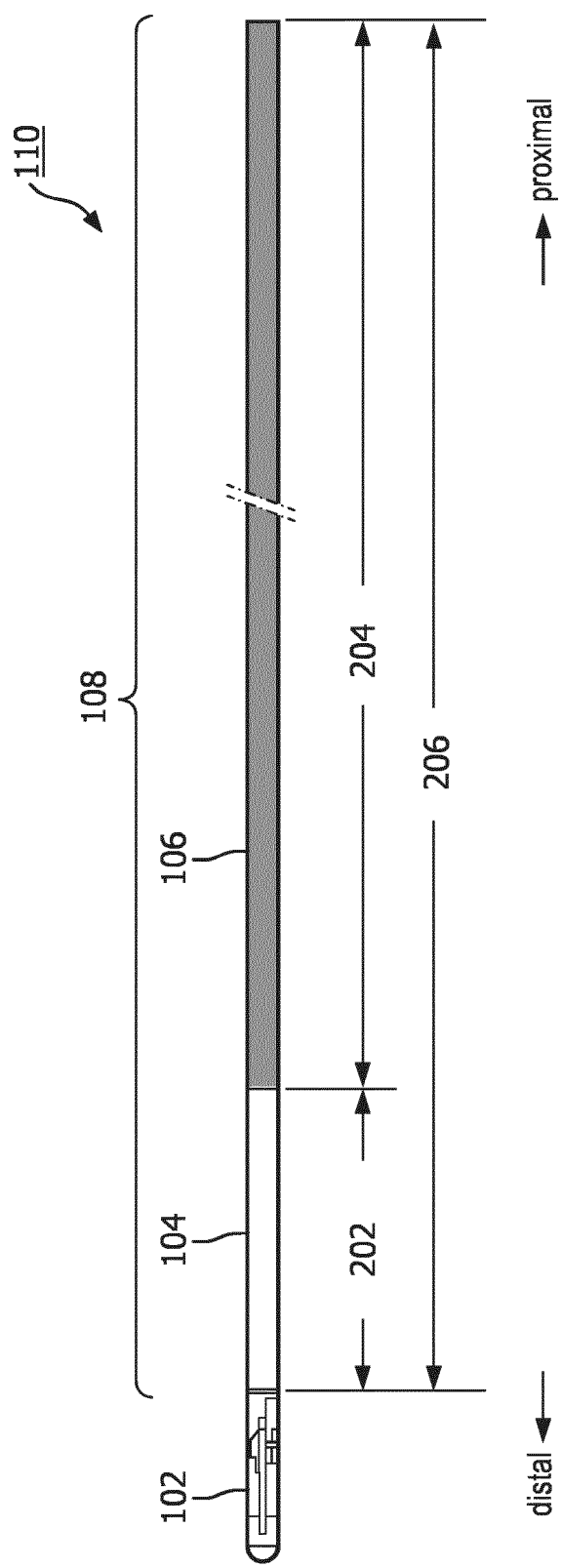
FIG. 2 is a schematic diagram of a portion of an ICE device according to embodiments of the present disclosure.

FIG. 2 is a schematic diagram of a portion of the ICE device 110 according to embodiments of the present disclosure. The tip assembly 102 and the flexible elongate member 108 are shaped and sized for insertion into vessels of a patient body. The flexible elongate member 108 can be composed of any suitable material, such as Pebax® polyether block amides. The distal portion 104 and the proximal portion 106 are tubular in shape and may include a primary lumen and one or more pullwire lumens extending longitudinally along the flexible elongate member 108. The primary lumen is sized and shaped to accommodate an electrical cable interconnecting the tip assembly 102 and the connector 124 for transferring echo signals obtained from the transducer elements. In some embodiments, the primary lumen can be shaped and sized to accommodate other components for diagnostic and/or therapy procedures. The pullwire lumens are sized and shaped to accommodate pullwires, for example, extending from the distal portion 104 to the handle 120. The pullwires may be coupled to the actuators 116 and the clutch 114 such that the flexible elongate member 108 and the tip assembly 102 are deflectable based on actuations of the actuators 116 and the clutch 114. In an embodiment, the primary lumen is shaped to facilitate alignment of the pullwire lumens. In addition, the tubular body of the flexible elongate member 108 may include a lined variable braided reinforcement layer configured to provide flexibility and kink resistance. The arrangements and configurations of the pullwires, the primary lumen, the pullwire lumens, the tip assembly 102, and the lined variable braided reinforcement layer are described in greater details herein. Dimensions of the flexible elongate member 108 can vary in different embodiments. In some embodiments, the flexible elongate member 108 can be a catheter having an outer diameter between about 8 and about 12 French (Fr) and can have a total length 206 between about 80 centimeters (cm) to about 120 cm, where the proximal portion 106 can have a length 204 between about 70 cm to about 118 cm and the distal portion 104 can have a length 202 between about 2 cm to about 10 cm.

Figure 3:
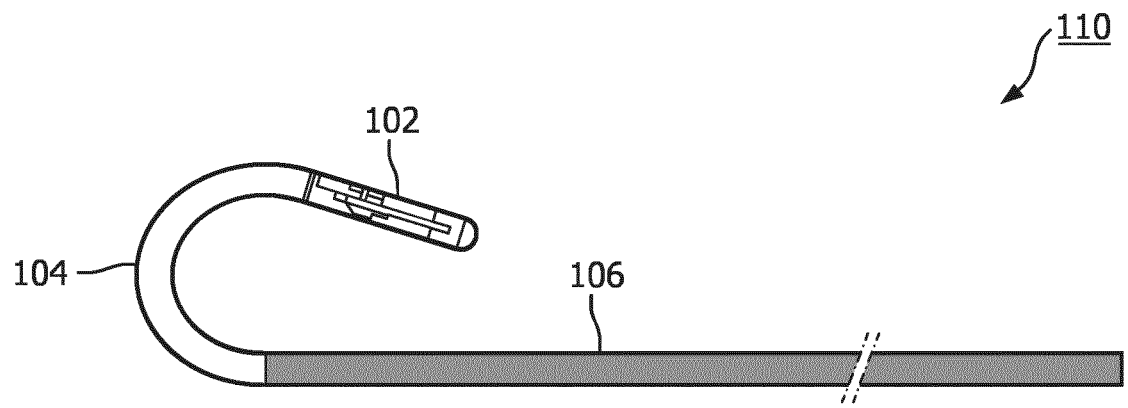
FIG. 3 is a schematic diagram of a portion of an ICE device under deflection according to embodiments of the present disclosure.

FIG. 3 is a schematic diagram of a portion of the ICE device 110 under deflection according to embodiments of the present disclosure. For example, the flexible elongate member 108 shown in FIG. 2 is referred to as a neutral position. In FIG. 3, the tip assembly 102 and the distal portion 104 of the flexible elongate member 108 are deflected from the neutral position.

Figure 4:
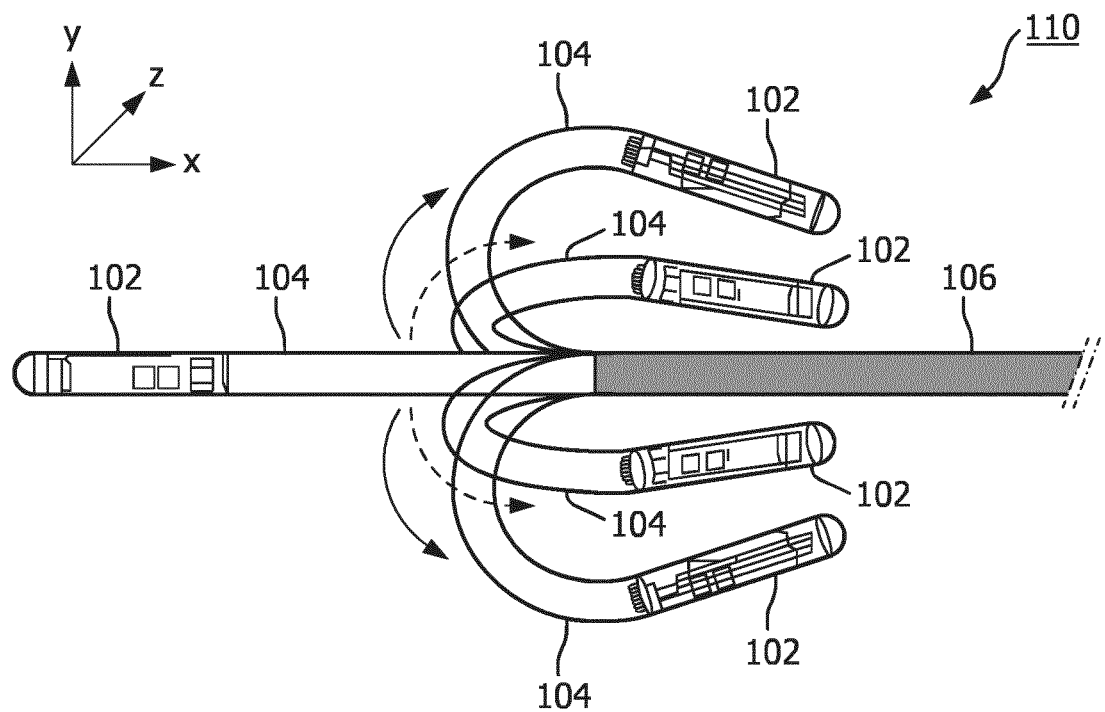
FIG. 4 is a schematic diagram illustrating deflections planes of an ICE device according to embodiments of the present disclosure.

FIG. 4 is a schematic diagram illustrating deflections planes of the ICE device 110 according to embodiments of the present disclosure. As shown, the tip assembly 102 and the distal portion 104 can be deflected along a first plane as shown by the solid arrows and a second plane as shown by the dotted arrows. In FIG. 3, the first plane is represented by an x-y plane and the second plane is represented by an x-z plane. For example, the x-y plane may correspond to a left-right plane and the x-z plane may correspond to an anterior-posterior plane for imaging the heart anatomy.

Figure 5:
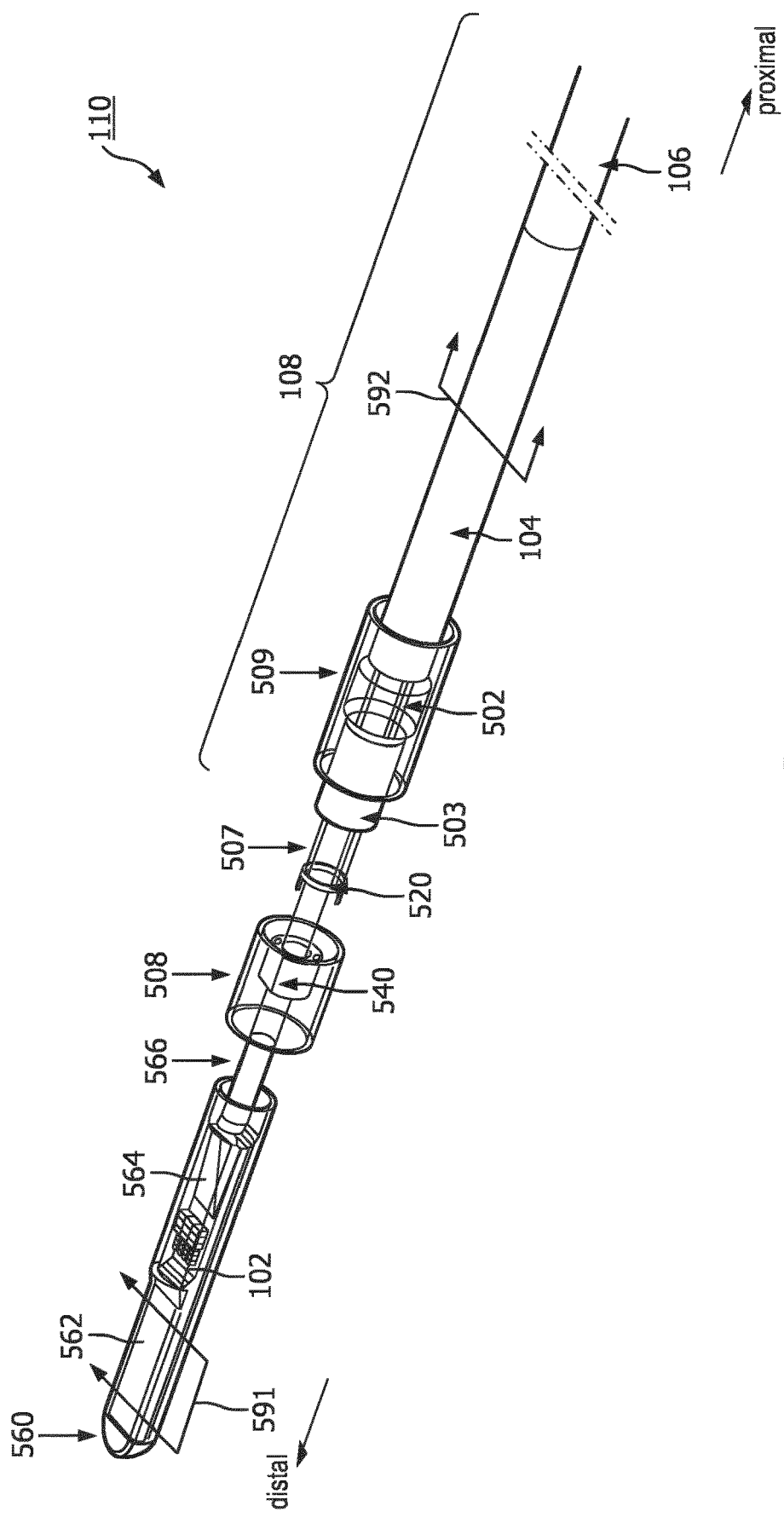
FIG. 5 is a schematic diagram illustrating an interconnection within an ICE device between a tip assembly and a flexible elongate member according to embodiments of the present disclosure.

FIG. 5 is a schematic diagram illustrating an interconnection within the ICE device 110 between the tip assembly 102 and the flexible elongate member 108 according to embodiments of the present disclosure. As shown, the interconnection between the tip assembly 102 and the distal portion 104 of the flexible elongate member 108 includes a crown element 520 and a sleeve element 540. The crown element 520 is coupled to the distal end of the distal portion 104. The sleeve element 540 is coupled to the crown element 520 and the proximal end of the tip assembly 102. The tip assembly 102 includes an imaging core 562 encased in a tip member 560. The tip assembly 102 can include an alignment portion (not shown) shaped to facilitate alignment during manufacturing, as described in greater detail herein. The imaging core 562 is connected to an electrical cable 566 via an electrical interconnection 564. The electrical cable 566 extends longitudinally along the flexible elongate member 108. The crown element 520 and the sleeve element 540 are fitted around the electrical cable 566.

The crown element 520 functions as an anchor for pullwires 507 such that the tip assembly 102 and the distal portion 104 may be deflectable upon actuations of the pullwires 507 in the proximal direction as shown in FIGS. 3 and 4 and described in greater detail herein. The sleeve element 540 functions as an alignment agent to align the crown element 520 and the pullwires 507 such that the deflection may provide predictable or predetermined articulation views.

In an embodiment, the flexible elongate member 108 may include a lined variable braided enforcement layer to provide flexibility and kink resistance as described in greater detail herein. In such an embodiment, the interconnection further includes a braid containment 502 positioned between an anchoring segment 503 and the distal end of the flexible elongate member 108. The braid containment 502 may be composed of material such as polyethylene terephthalate (PET) or any suitable material. The anchoring segment 503 can be composed of similar material as the flexible elongate member 108. The braid containment 502 functions as a termination for the braided reinforcement layer. The braid containment 502 encases the termination of the materials (e.g., stainless steel wires) of the braided reinforcement layer to prevent exposure of the materials outside of the ICE device 110. The structure of the flexible elongate member 108 and the braided reinforcement layer are described in greater detail herein. The anchoring segment 503 couples the braid containment 502 to the crown element 520 and the sleeve element 540 to allow for thermal reflow when bonding the components at the interconnection.

The interconnection may further include support members 508 and 509, which are thin sleeves, to provide protection over connections of different components. The support members 508 and 509 may be composed of any suitable polymeric material. As shown, the support member 508 is positioned over the connections among the sleeve element 540, the tip assembly 102, the crown element 520, and the anchoring segment 503. The support member 509 is positioned over the connections among the braid containment 502, the anchoring segment 503, and the distal portion 104 of the flexible elongate member 108.

Figure 6:
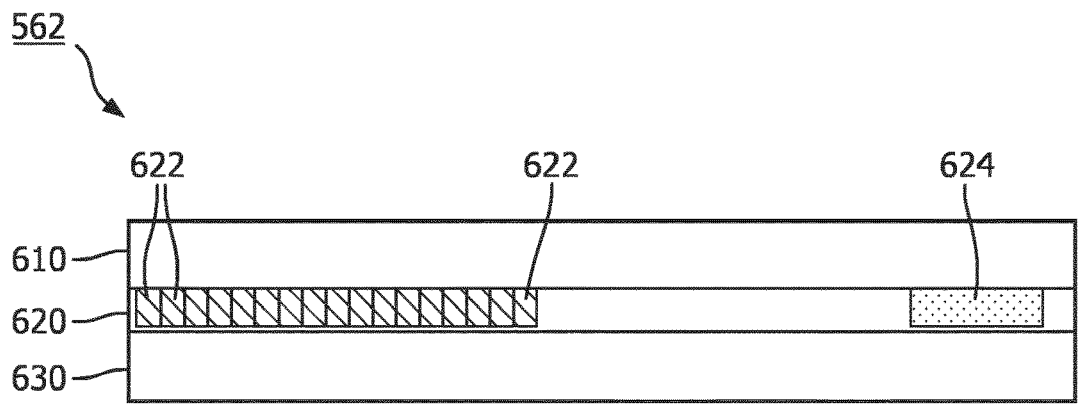
FIG. 6 is a cross-sectional side view of an imaging core according to embodiments of the present disclosure.

FIG. 6 is a cross-sectional side view of the imaging core 562 taken along the line 591 of FIG. 5 according to embodiments of the present disclosure. The imaging core 562 can include a transducer circuit layer 620 embedded between an acoustic stack 610 and a backing material layer 630. The transducer circuit layer 620 includes an array of ultrasound transducer elements 622 coupled to one or more multiplexer chips 624, for example, via conductive traces and/or associated circuitry. In some embodiments, the number of ultrasound transducer elements 622 may be 8, 16, 32, 64, or any suitable number. The ultrasound transducer elements 622 are composed of piezoelectric material. Exemplary transducers for ICE have a typical thickness of approximately 0.28 mm in the piezoelectric material to enable an 8 megahertz (MHz) ultrasound signal to be generated and transmitted at a typical velocity of 1500 meter per second (m/sec) through blood. The transducer thickness can be of various thicknesses ranging approximately from 0.56 mm to 0.19 mm to generate sufficient penetration depth in tissue imaging. In general, the thickness of the transducers can be adjusted for the frequency of sound in the transmission medium for the desired penetration depth in any tissue imaging. Image intensity can be adjusted by driving voltage on the transducers.

The multiplexer chips 624 multiplex control signals, for example, generated by the processing system 130, and transfer the control signals to corresponding ultrasound transducer elements 622. The controls signals can control the emission of ultrasound pulses and/or the reception of echo signals. In the reverse direction, the multiplexer chips 624 multiplexes echo signals reflected by target tissue and received by the ultrasound transducer elements 622 multiplexer chips 624 and transfer the received echo signals, for example, to the processing system 130 for processing and/or display.

The acoustic stack 610 is composed of materials acoustically matched to the ultrasound transducer elements 622, the transmission medium (e.g., the tip member 560 and the patient body), and the target tissue for imaging. The backing material layer 630 is composed of an acoustically absorptive material so that the backing material layer 630 can absorb or deaden the ultrasonic waves coming from the back of the ultrasound transducer elements 622. In some embodiments, one or more components (e.g., transducer elements 622, chip 624, electrical cables, etc.) of the imaging core 562 can be coupled to the flexible elongate member 108. In some embodiments, one or more components of the imaging core 562 can be positioned within the flexible elongate member 108.

Figure 7:
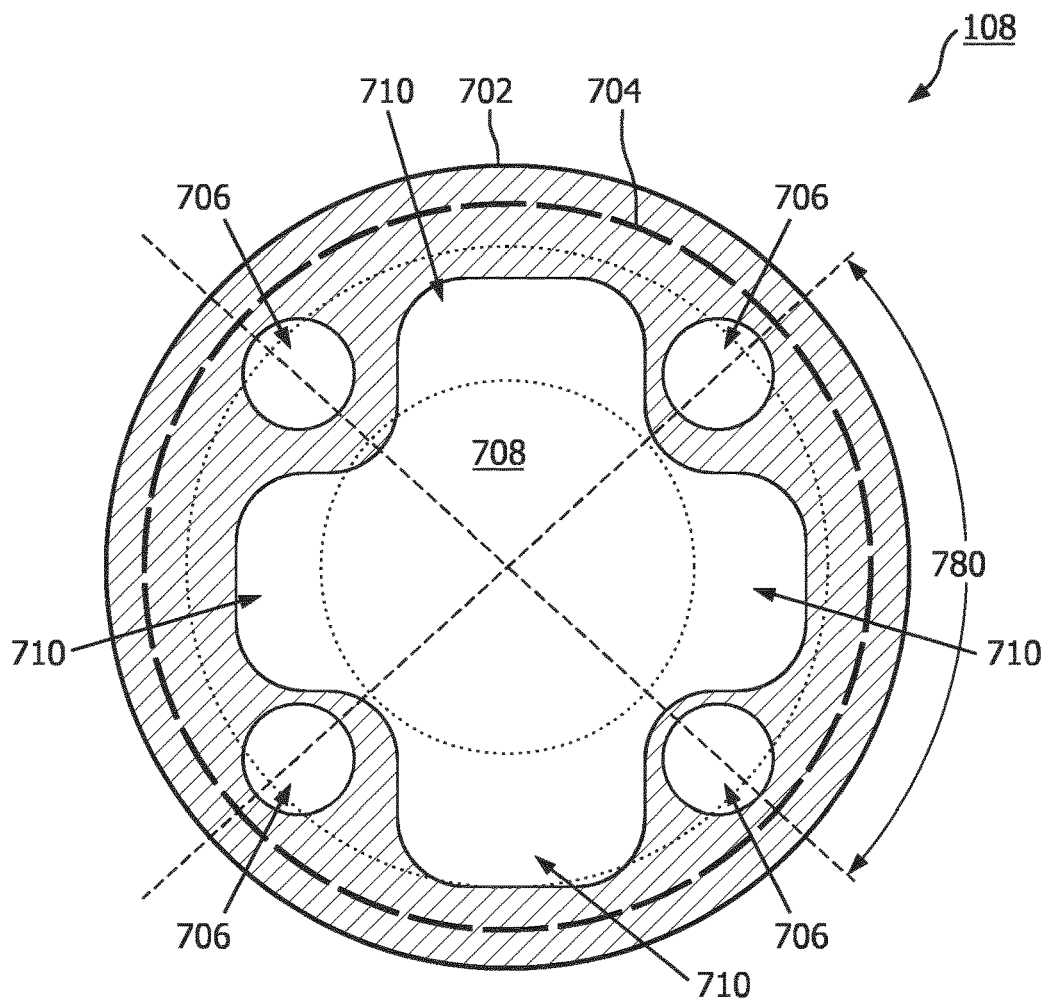
FIG. 7 is a cross-sectional view of a lined variable braided differential durometer multi-lumen catheter shaft according to embodiments of the present disclosure.

FIG. 7 is a cross-sectional view of the flexible elongate member 108 taken along the line 592 of FIG. 5 according to embodiments of the present disclosure. The flexible elongate member 108 has a tubular body including a tubular wall 702, a central lumen 708, and a plurality of secondary lumens 706 extending between a distal end and a proximal end of the flexible elongate member 108. The central lumen 708 has a rounded cross-shaped cross-sectional profile. The arms 710 of the cross-shaped cross section form recesses that can anchor the angular positions of the secondary lumens 706. For example, the secondary lumens 706 are positioned between adjacent arms 710 during manufacturing. The secondary lumens 706 are shaped and sized to accommodate pullwires such as the pullwires 507. Thus, the secondary lumens 706 are also referred to as pullwire lumens. The secondary lumens 706 are positioned within the tubular wall 702 radially spaced apart by an angle 780 of about 90 degrees. For example, the pullwires 507 may be threaded through the secondary lumens 706 and coupled to the actuators 116 at the handle 120. Thus, the actuators 116 may be configured to control or place tensions at the pullwires 507 to bend the tip assembly 102 and the distal portion 104 as shown in FIGS. 3 and 4.

In an embodiment, the central lumen 708 and the secondary lumens 706 can be lined with a lubricious lining material (not shown) such as a polytetrafluoroethylene (PTFE) material. The lining material creates frictionless surfaces for threading, delivery, and actuations of pullwires or any other suitable diagnostic sensor assembly. In addition, the lining material can function as a support structure to prevent the central lumen 708 and the secondary lumens 706 from collapsing. Further, the lining material can function as a bather to protect abrasion caused by the frequent shifting or actuations of the pullwires and/or threading of the other diagnostic sensor assembly.

In an embodiment, the flexible elongate member 108 can include a layer of braided element 704 disposed within the tubular wall 702. The braided element 704 can be composed of any suitable material and geometry. For example, the braided element 704 may include stainless steel flat wires, which may provide optimal usage of radial space and additional strength. The braided element 704 is braided with pitches that vary along a longitudinal length of the flexible elongate member 108. The braids can include any suitable braid pattern. The braid pattern may be selected to improve torque transmission, pushability, and/or kink resistance. In some embodiments, the braided element 704 may include braids with a higher per inch count (PIC) at the distal portion 104 than at the proximal portion 106 so that the distal portion 104 is more flexible than the proximal portion 106. In addition, the braided element 704 may include braids with varying PICs around the junction at which the distal portion 104 meets the proximal portion 106.

In an embodiment, the tubular wall 702 of the flexible elongate member 108 may be composed of materials of different durometers at the distal portion 104 and the proximal portion 106 to further improve steerability and kink resistance. For example, the tubular wall 702 may be composed of a low durometer material at the distal portion 104 and a high durometer material at the proximal portion 106 without any transition region. Thus, the flexible elongate member 108 can be relatively rigid at the proximal portion 106, but substantially pliable or flexible at the distal portion 104.

Figure 8:
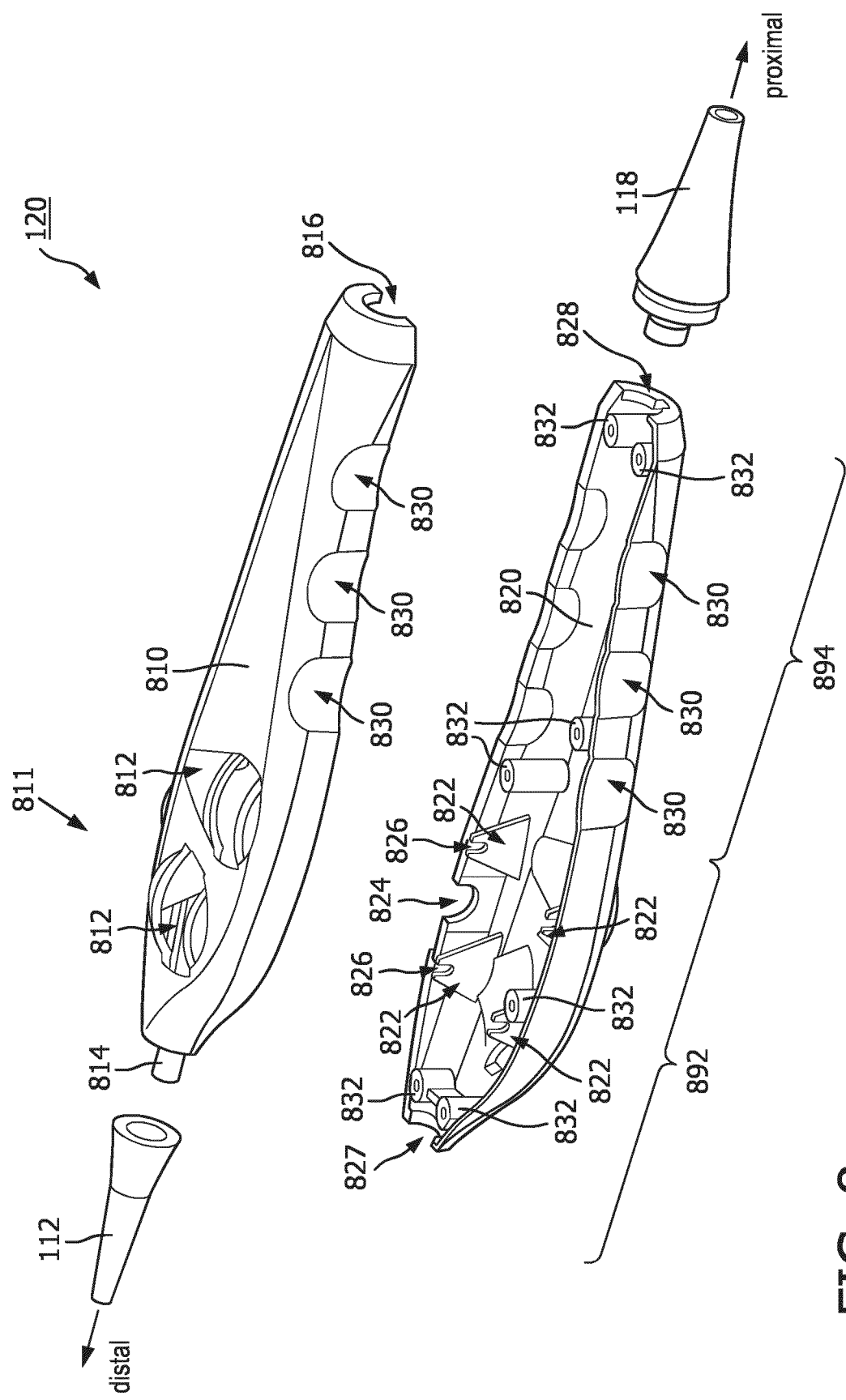
FIG. 8 is a diagrammatic exploded perspective view of a handle according to embodiments of the present disclosure.

FIG. 8 is a perspective view of some components of the handle 120 according to embodiments of the present disclosure. The embodiment of FIG. 8 includes features similar to those shown and described with respect to FIG. 1. It is understood that the handle 120 can include additional components, such as those described with respect to FIGS. 9-16, for example. Features of the handle 120 illustrated in FIG. 8 can also be seen in FIGS. 11, 12, and 18-20, for example.

Referring to FIG. 8, the handle 120 includes an upper shell 810 and a bottom shell 820. The upper shell 810 and the bottom shell 820 can have matching clamp design. During assembly, the shells 810, 820 can be positioned in contact with one another and fastened together via mechanical snap-ons, screws, adhesives, and/or other suitable mechanism. The upper shell 810 and the bottom shell 820 can be composed of any suitable material, including a plastic, plastic composite material, polymer, for example. In one embodiment, the upper shell 810 and the bottom shell 820 can be constructed using acrylonitrile butadiene styrene (ABS). Any suitable manufacturing process can be used, including injection molding, for example. The upper shell 810 and the bottom shell 820 together form an elongate housing 811 including a distal portion 892 and a proximal portion 894. The elongate housing 811 extends in a direction parallel to a longitudinal axis of the device 110.

Figure 9:
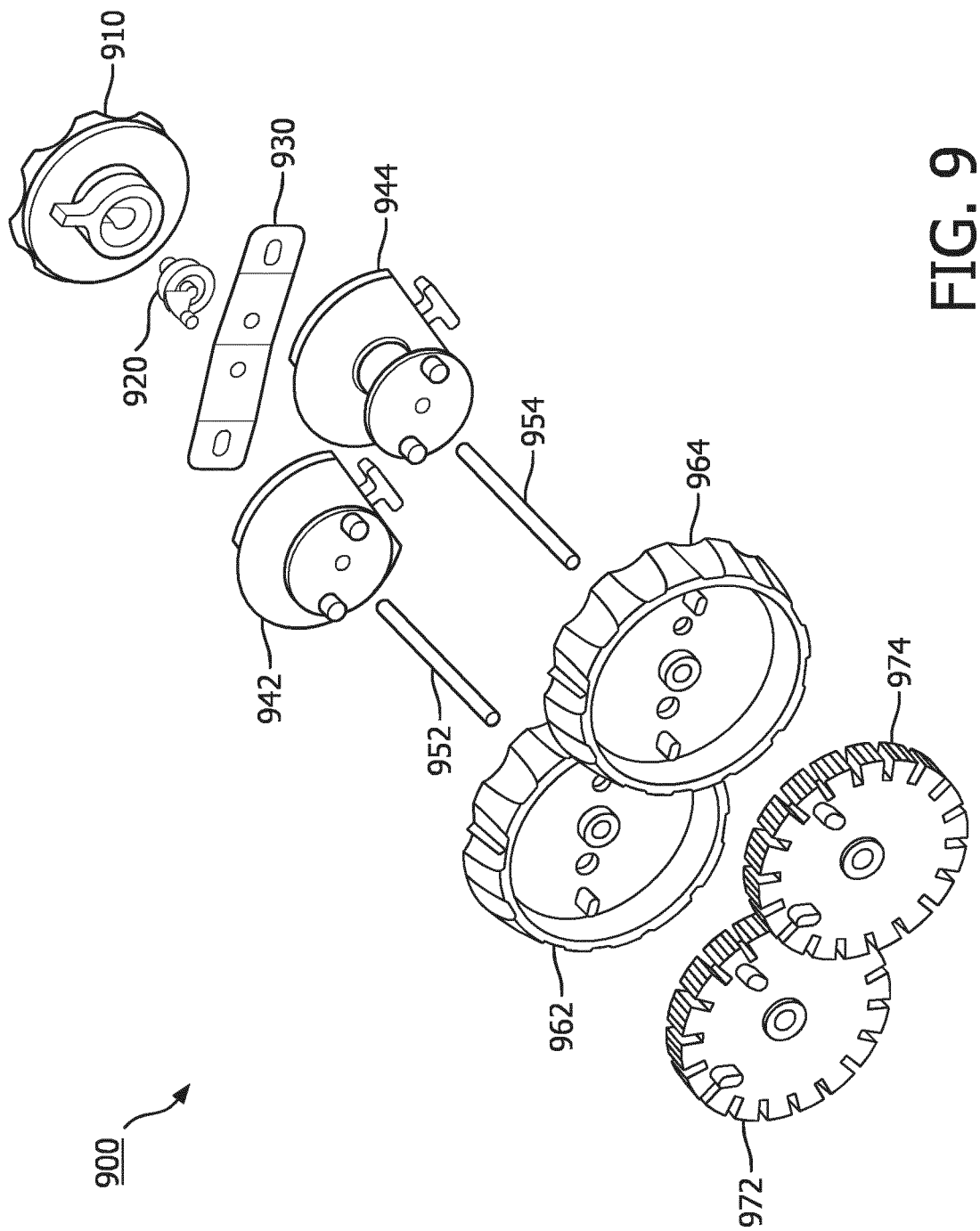
FIG. 9 is a diagrammatic exploded perspective view of steering and/or clutch mechanism configured to be positioned within a handle according to embodiments of the present disclosure.

The interval cavities of the upper shell 810 and the bottom shell 820 are structured to accommodate steering control components. For example, the actuators 116, the clutch 114, and other steering-related components can be positioned at the distal portion 892. As shown, the bottom shell 820 includes a plurality of alignment members 822 at the distal portion 892. The alignment members 822 include notches or cutouts 826 for aligning the steering control components, such as the axles 952, 954 (FIG. 9). Referring again to FIG. 8, the alignment members 822 may be triangular or any suitable shape. A slot 824 at the distal portion 892 of the bottom shell 820 is shaped to accommodate mounting of the clutch 114 (FIG. 1). The upper shell 810 may include alignment members similar to the alignment members 822 and a slot similar to the slot 824 aligned to the positions of the alignment members 822 and the slot 824 at the bottom shell 820. In addition, the upper shell 810 includes open slots 812 shaped to expose portions of top control surfaces of the actuators 116 when the actuators 116 are mounted lengthwise in the housing 811 as shown in FIG. 1. The bottom shell 820 can also include open slots 812 in some embodiments. Thus, top and bottom controls surfaces of the actuators 116 can be exposed when the actuators 116 are mounted lengthwise in the housing 811. Thus, a physician or clinician may manipulate or rotate the actuators 116 and the clutch 114, for example, using a thumb or a finger, while holding the handle 120 for steering. The steering control components and mechanisms are described in greater detail herein.

The outer surfaces of the upper shell 810 and the bottom shell 820 are ergonomically shaped to allow single-handed control of the handle 120. As shown, the outer surfaces include a plurality of finger-shaped grooves 830 at the proximal portion 894. The finger-shaped grooves 830 may provide a user with grip stability while the user manipulates the actuators 116 and/or the clutch 114 using other fingers (e.g., a thumb and an index finger).

The internal cavities of the upper shell 810 and the bottom shell 820 can further include support members 832 to facilitate attachment of the shells 810, 820 to one another. For example, support member 832 can include recesses including screw threads that receiving screws to join the shells 810, 820 together.

The upper shell 810 further includes a tubular connection member 814 at the distal end and a slot 816 at the proximal end. The bottom shell 820 further includes a slot 827 at the distal end and a slot 828 at the proximal end. When the upper shell 810 is assembled with the bottom shell 820, the tubular connection member 814 is fitted into the slot 827, and the slots 816 and 828 form a proximal opening. The tubular connection member 814 may be coupled to the strain relief 112. For example, the outer diameter of the tubular connection member 814 is sized to fit into the inner diameter of the strain relief 112. The proximal opening may be sized and shaped to accommodate the strain relief 118. For example, when assembled in the device 110, the strain reliefs 112 and 118 couples the handle 120 to the flexible elongate member 108 and the electrical cable 122, respectively. The handle 120 receives the pullwire segments 507 extended through the secondary lumens 706. The pullwire segments 507 are coupled to the steering control components disposed within the handle 120. The handle 120 passes the electrical cable 566 through the housing 811 to the strain relief 118. The cable 122 may include the electrical cable 566 between the strain relief 118 and the connector 124. Strain reliefs 112, 118 can be made of a flexible material such as a thermoplastic elastomer, which is compatible with standard sterilization methods. In some embodiments, strain reliefs 112, 118 are over-molded onto the proximal shaft 106 for a stronger bond and a smoother transition between handle 120 and proximal shaft 106. The strain reliefs 112, 118 can be made of a material configured to be over-molded.

FIG. 9 is an exploded perspective view of a steering control configuration 900 according to embodiments of the present disclosure. The handle 120 may employ the configuration 900 to provide steering control for the device 110. The configuration 900 includes a clutch control member 910, a clutch cam 920, a clutch spring 930, pulleys 942 and 944, axles 952 and 954, actuation control members 962 and 964, and frictional members 972, 974. In some embodiments, the components in the configuration 900 can be directly or indirectly coupled to one another when the handle 120 is assembled. In some embodiments, the components of the configuration 900 can be positioned adjacent to and/or in contact with one another when the handle 120 is assembled. For example, the components of the configuration 900 may be arranged within the handle 120 to mechanically engage one another. The axle 952 extends through respective bores in the clutch spring 930, the pulley 942, the actuation control member 962, and the frictional member 972. The axle 954 extends through respective bores in the clutch spring 930, the pulley 944, the actuation control member 964, and the frictional member 974. The axles 952, 954 can be formed of any suitable material, including a metal or metal alloy. The pulleys 942, 944 and the actuation control members 962, 964 rotate around the axles 952, 954. The axles 952, 954 also help center the clutch spring 930.

The components of the configuration 900 can be made of any suitable material(s). For example, the axles 952 and 954 and the clutch spring 930 can be composed of any suitable material such as metal and constructed using machining or stamping techniques. The clutch control member 910, the clutch cam 920, the pulleys 942 and 944, the actuation control members 962 and 964, and the frictional members 972, 974 can be composed of any suitable materials such as plastic or polymeric material. These components can be manufactured using any suitable process, such as 3D printing and injection molding, for example.

The pulleys 942 and 944, the axles 952 and 954, and the actuation control members 962 and 964 operate together to provide mechanisms for controlling the bending of the ICE device 110 as shown in FIGS. 3 and 4. For example, a pair of pullwire segments 507 that controls the bending in an anterior-posterior plane may be wrapped around the pulley 942 and another pair of pullwire segments 507 that controls the bending in a left-right plane may be wrapped around the pulley 944. When coupled in position, the actuation control member 962 rotates around the axle 952, causing the pulley 942 to rotate and apply tension to a pullwire 507 controlling the bending in the anterior-posterior plane. Similarly, the actuation control member 964 rotates around the axle 954, causing the pulley 944 to rotate and apply tension to a pullwire 507 controlling the bending in the left-right plane. The pulleys 942 and 944, the actuation control members 962 and 964, and the coupling of the pullwires 507 are described in greater detail herein. In some embodiments, one or more of the pulley 942, 944 and one or more of the actuation control members 962, 964 are collectively referenced as one or more respective steering actuators. While rotation of the actuation control members 962 and 964 is described, it is understood that any suitable type of actuation is contemplated, such as translation, movement along an arc, depression of a button, etc.

Generally, when the physician removes his or her finger from the actuation control members 962, 964, the tip assembly 102 and the distal portion 104 return to their quiescent, non-deflected state. When the physician maintains force with his or her finger on the actuation control members 962, 964, the tip assembly 102 and the distal portion 104 remain in their deflected state.

The clutch control member 910, the clutch cam 920, the clutch spring 930, and the frictional members 972, 974 operate together to form a variable braking systems to provide feedback resistance to a user manipulating the actuation control members 962 and/or 964 and locking mechanisms to lock the positions of the actuation control members 962 and 964 when a desired articulation view is achieved. In that regard, the clutch control member 910 can be selectively moved, such as by rotation, to control the resistance of the actuation control members 962, 964 to movement. When the clutch control member 910 is moved in a first direction (e.g., clockwise rotation), the resistance increases. Thus, when the user removes his or her finger from the actuation control members 962, 964, the tip assembly 102 and the distal portion 104 return to their quiescent state in a relatively slower manner. A brake is applied to the actuation control members 962, 964 in the sense that they return to their non-deflected state more slowly. When coupled in position, an adjustment or rotation of the clutch control member 910 in the first direction causes the clutch cam 920 to press against the clutch spring 930, resulting in a compression force towards the pulleys 942 and 944 and pushing the actuation control members 962 and 964 against the frictional members 972, 974. The frictional members 972, 974 may be referenced as frictional in that they operate based on contact with the actuation control members 962, 964 that results in friction between the touching components. The outer circumference of the frictional members 972, 974 are structured to create frictional contacts with the actuation control members 962 and 964 in order to provide feedback resistance or locking the rotational positions of the actuation control members 962 and 964 as described in greater detail herein.

When the clutch control member 910 is moved in a second direction (e.g., counterclockwise rotation), the resistance decreases. Thus, when the user removes his or her finger from the actuation control members 962, 964, the tip assembly 102 and the distal portion 104 return to their quiescent state in a relatively faster manner When coupled in position, an adjustment or rotation of the clutch control member 910 in the second direction contact between the clutch cam 920 and the clutch spring 930 to lessen, resulting in reduction of compression force towards the pulleys 942 and 944. Thus, the actuation control members 962 and 964 are pressed to a lesser extent against the frictional members 972, 974. The outer circumferential surface of the frictional members 972, 974 is designed to allow the actuation control members 962, 964 to rotate freely while the clutch/brake is off and to be restrictive when the clutch/brake is on.

In some embodiments, increasing the compression force on the clutch mechanism makes rotation of the actuation control members 962, 964 more difficult. Thus, the user must apply more force to move the actuation control members 962, 964 to deflect the the tip assembly 102 and the distal portion 104. Similarly, when less or no compression force is applied to the clutch mechanism, rotation of the actuation control members 962, 964 is relatively easier. Thus, the user can apply less force to move the actuation control members 962, 964 to deflect the the tip assembly 102 and the distal portion 104.

In some embodiments, one or more of the components in the configuration 900 can be larger in size (e.g., diameter) than a corresponding component. For example, the frictional member 972 can be larger than the frictional member 974. The actuation control member 962 can be larger than the actuation control member 964. The pulley 942 can be larger than the pulley 944. In other embodiments, corresponding components are similar sizes. For example, the frictional members 972, 974 can have equal diameters, the actuation control members 962, 964 can have equal diameters, and/or the pulleys 942, 944 can have equal diameters.

Figure 10B:
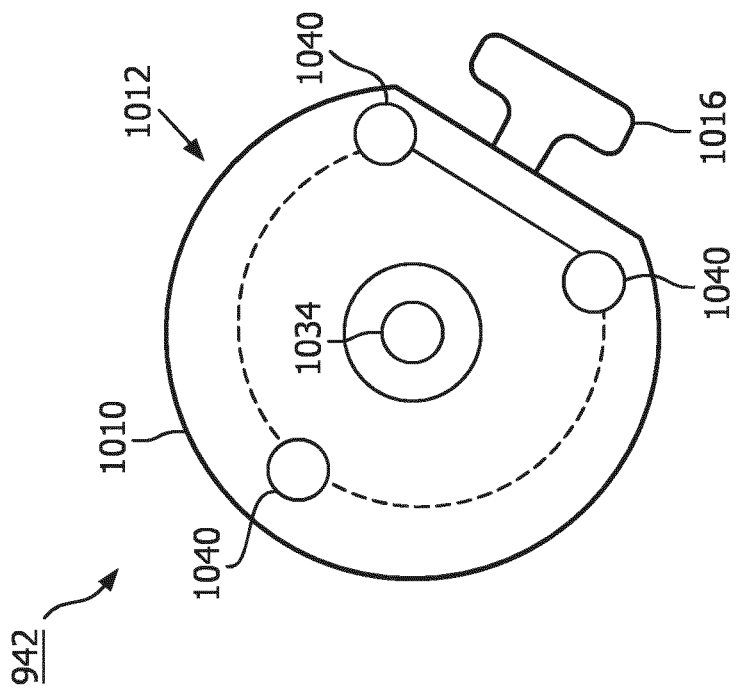
FIG. 10B is a diagrammatic end view of the pulley of FIG. 10A.
Figure 10A:
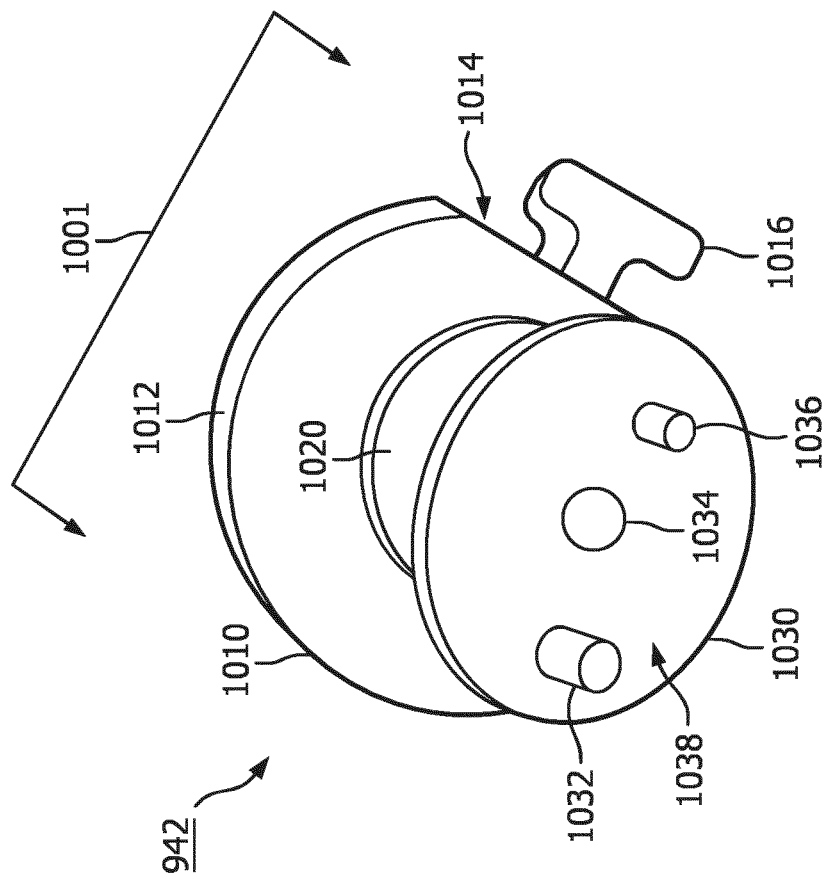
FIG. 10A is a diagrammatic perspective view of pulley of a steering mechanism according to embodiments of the present disclosure.

FIG. 10A is a perspective view of the pulley 942 according to embodiments of the present disclosure. The pulley 942 includes a base disc 1010 coupled to a top disc 1030 via a tubular connecting member 1020. The base disc 1010 includes an open groove 1012 and an anchoring member 1016. The anchoring member 1016 may be T-shaped in some embodiments. The open groove 1012 is positioned along at least a portion of an outer circumference of the base disc 1010. The top disc 1030 includes posts 1032 and 1036 and an opening 1034. The opening 1034 extends longitudinally or axially through the body of the pulley 942, for example, through the connecting member 1020 and the based disc 1010. The axle 952 extends through the opening 1034. The posts 1032 and 1036 protrude from a surface 1038 of the top disc 1030. The posts 1032 and 1036 are received within respective bores of the actuation control member 962 when the handle 120 is assembled. The actuation control member 962 can be coupled to the pulley 942 when the posts 1032, 1036 are received within the respective bores. That is, movement of the actuation control member 962 causes corresponding movement of the pulley 942 and the tip assembly 102 and the distal portion 104. In some embodiments, the posts 1032 and 1036 may have different diameters to facilitate alignment to the actuation control member 962. As described in greater detail with respect to FIGS. 12 and 13, a pair of pullwire segments 507 wraps around the open groove 1012 and are tied to the anchoring member 1016. The pulley 944 has similar features as the pulley 942. In some embodiments, the size of the pulley 942, such as a diameter of the base disc 1010, is larger than the pulley 944.

FIG. 10B is a back view of the pulley 942 viewing in a direction as shown by the line 1001 according to embodiments of the disclosure. The pulley 942 includes openings or holes 1040 that are radially spaced around a circumference of the base disc 1010. The openings 1040 are disposed on a side of the pulley 942 opposite the posts 1032, 1036. The openings 1040 can be in communication with the open groove 1012 such that the pullwire segments 507 can extend from the groove 1012 through the openings 1040 to the anchoring member 1016.

Figure 11:
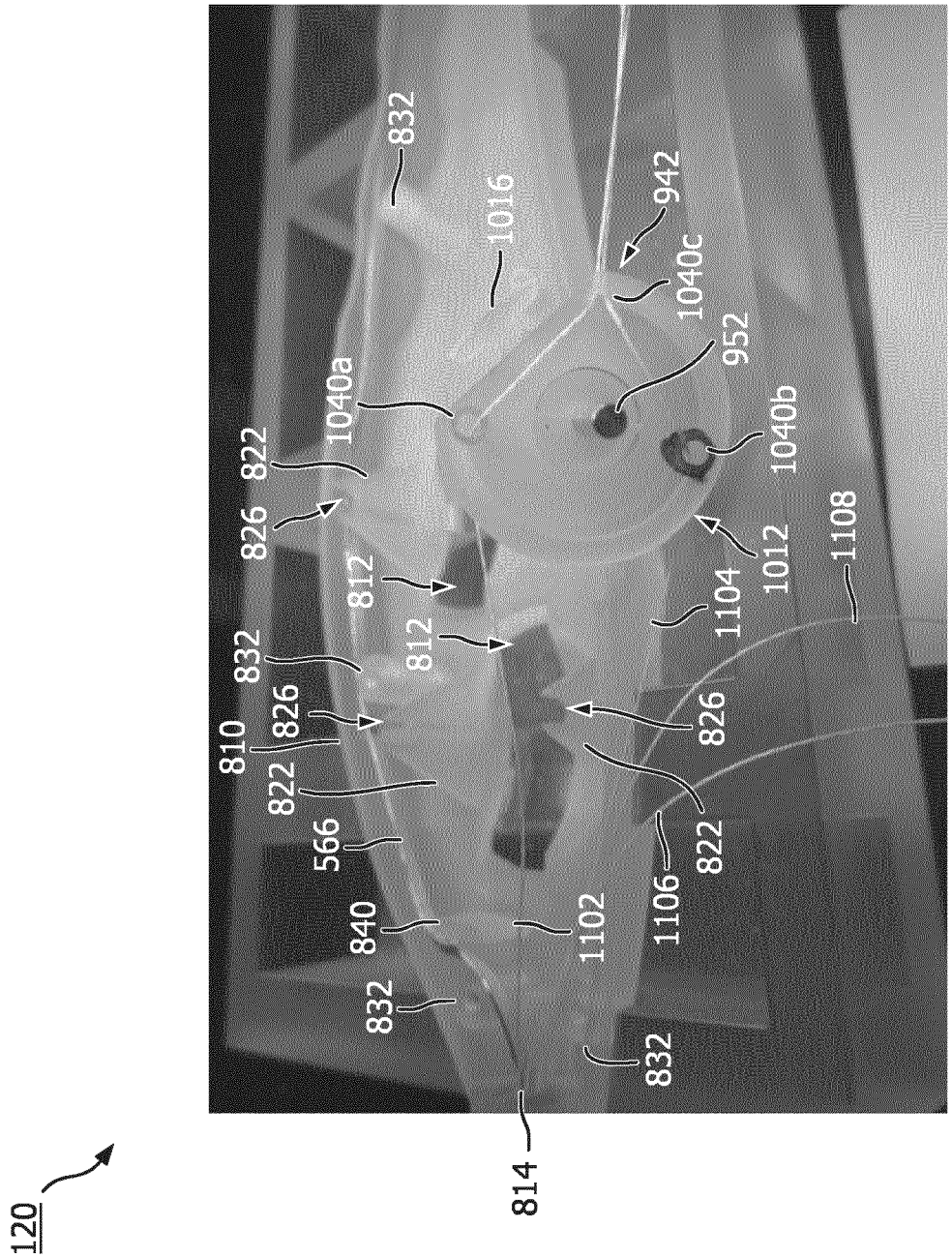
FIG. 11 is a perspective view of a handle including pullwire segments coupled to a pulley according to embodiments of the present disclosure.
Figure 12:
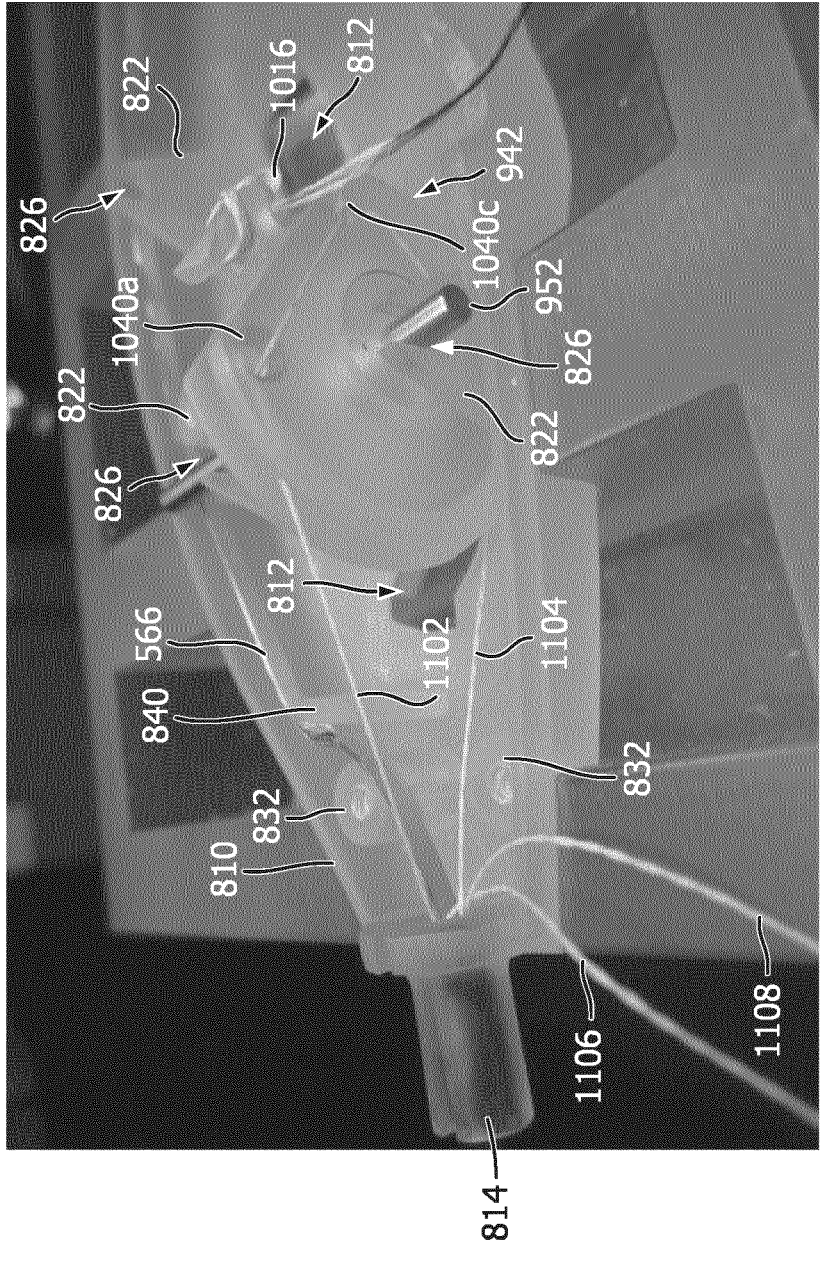
FIG. 12 is a perspective view of a handle including pullwire segments coupled to a pulley according to embodiments of the present disclosure.

FIGS. 11 and 12 are perspective views of the handle 120. FIGS. 11 and 12 include components of the handle 120 that are similar to those described with respect FIGS. 8-10B, for example. FIGS. 11 and 12 include pullwire segments 1102, 1104, 1106, and 1108, which are similar to the pullwire segments 507. In that regard, the pullwire segments 1102, 1104, 1106, and 1108 can be more proximal portions of the pullwire segments 507. FIGS. 11 and 12 also illustrate exemplary steps in a method of assembling the ICE device 110. The steps illustrated in FIGS. 11 and 12 can be references as the pullwire termination process. FIG. 11 shows pullwire segments 1102 and 1104 positioned within the open groove 1012 of the pulley 942. From respective portions of the open groove 1012, the pullwire segment 1102 extends through the opening 1040*a* and the pullwire segment 1104 extends through the opening 1040*b*. Both pullwire segments 1102, 1104 extend through the opening 1040*c*. The pullwire segments 1102, 1104 can be twisted together after they extend through the opening 1040*c*.

FIG. 12 shows the proximal portions of pullwire segments 1102, 1104 being tied around the anchoring member 1016 after being threaded through the opening 1040c. Any suitable knot can be used to affix the pullwire segments 1102, 1104 to the anchoring member 1016. After knot terminations, adhesive can be applied at one or more points within the handle 120 (unifying hole 1040c, anchoring member 1016, etc.), to further strengthen the attachment of the pullwire segments to the pulleys. Because the pullwire segments 1102, 1104 are tied to the pulley 942 at the proximal portion of the device 110, and tied to the crown member 520 at the distal portion of the device 110, movement of the actuation member 962 creates tension in the pullwire segments 1102, 1104 and deflects the tip assembly 102 and the distal portion 104. Similar steps can be carried out to attach the pullwire segments 1106, 1108 to the pulley 944.

FIGS. 11 and 12 additionally show a routing member 840 of the handle 120. The routing member 840 orients or reorients the coaxial cable 566 so that the cable is spaced from the pullwire segments 1102, 1104, 1106, 1108 within the handle 120. In that regard, the coaxial cable 566 and the pullwire segments 1102, 1104, 1106, 1108 enter the handle via the tubular connection member 814. The routing member 840 directs the coaxial cable away from the plurality of pullwire segments 1102, 1104, 1106, 1108 such that assembly and/or operation of the components of the configuration 900 does not interfere with the coaxial cable 566. The routing member 840 can work in cooperation with the support members 832 and the alignment members 822 to position the cable 556 along an inner perimeter of the handle 120. In that regard, the support members 832 and the alignment members 822 can be referenced as routing members 840, in some embodiments.

Figure 13:
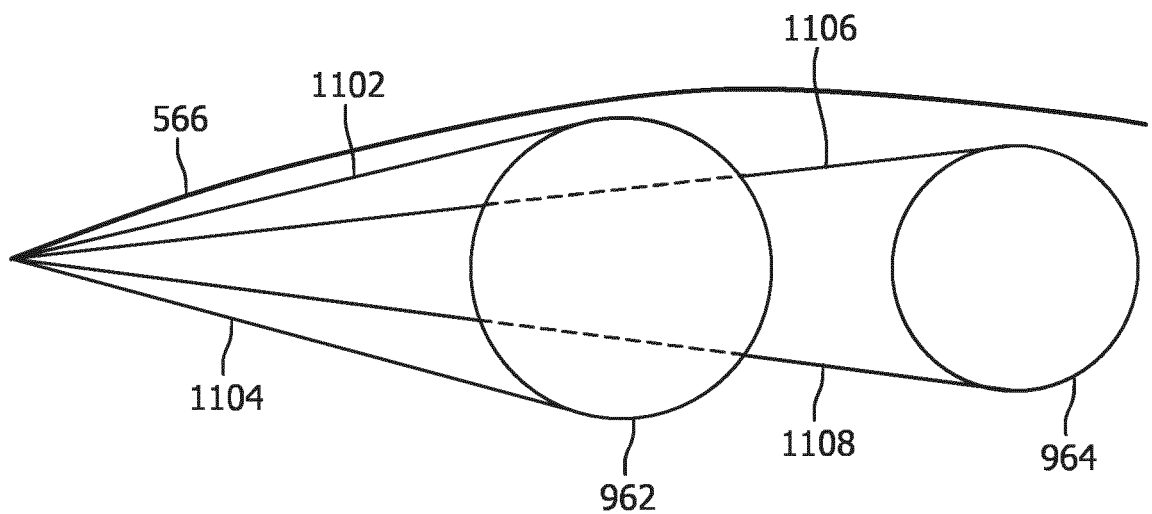
FIG. 13 is a diagrammatic schematic view illustrating relationships between pullwire segments and actuation control members according to embodiments of the present disclosure.

FIG. 13 is a diagrammatic schematic illustration of how the pullwire segments 1102, 1104, 1106, 1108 interact with actuation control members 962, 964. In that regard, it is understood that the pullwire segments 1102, 1104, 1106, 1108 are directly coupled to the pulleys 942, 944. The actuation control members 962, 964 are coupled to the pulleys 942, 944, respectively, such that movement of the actuation control members 962, 964 causes movements of the pulleys 942, 944 and the pullwire segments 1102, 1104, 1106, 1108. Thus, the components indicated by reference numerals 962, 964 can be representative of the actuation control members 962, 964 and/or the pulleys 942, 944. As shown the cable 566 is spaced from the pullwire segments 1102, 1104, 1106, 1108. Movement of the pullwire segments 1102, 1104, 1106, 1108 need not affect the cable 566. While the actuation control member 962 is larger than the actuation control member 964 in FIG. 13, it is understood that the actuation control member 964 can be larger than the actuation control member 962 or the actuation control members 962, 964 can have the same size, such as the same diameter.

In an exemplary embodiment, the actuation control member 962 can control movement of the tip assembly 102 and the distal portion 104 along the anterior-posterior plane. For example, the pullwire segment 1102 can be associated with anterior movement, and the pullwire segment 1104 can be associated with posterior movement. In an exemplary embodiment, the actuation control member 964 can control movement of the tip assembly 102 and the distal portion 104 along the right-left plane. For example, the pullwire segment 1106 can be associated with right movement, and the pullwire segment 1108 can be associated with left movement. The components of the configuration 900, including the actuation control members 962, 964, the pulleys 942, 944, and the pullwire segments 1102, 1104, 1106, 1108 can be positioned within the handle 120 such that movement of one of the actuation control member 962, 964 does not affect movement of the other actuation control member 962, 964.

In an exemplary embodiment, the ICE device 110 includes two pullwires. Each pull wires can include two segments. That is, each pull wire can be arranged to split into two segments. For example, a first pullwire can include pullwire segments 1102, 1106. In such embodiments, the first pullwire can include the segments 1102, 1106 associated with anterior and right movement. A second pullwire can include pullwire segments 1104, 1108. That is, the first pullwire can include the segments 1104, 1108 associated with posterior and left movement.

Figure 14:
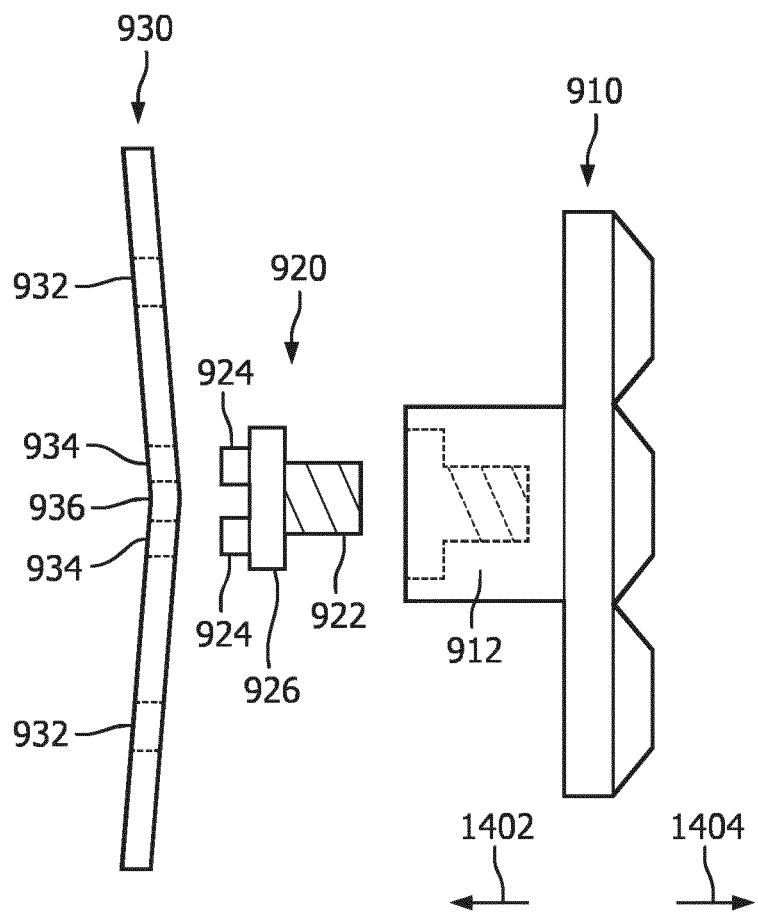
FIG. 14 is a diagrammatic side view of a clutch control member, a clutch cam, and a clutch spring according to embodiments of the present disclosure.

FIG. 14 is an exploded side view of a clutch mechanism including the clutch control member 910, the clutch cam 920, and the clutch spring 930. The clutch mechanism allows a user to control how quickly or slowly the tip assembly 102 and the distal portion 104 return to their non-deflected state after a user reduces the force applied to the actuation control members 962, 964. The clutch control member 910 can be moved, such as by rotation, through a continuous series of positions to control the resistance of the actuation control members 962, 964. That is, the user can select different speeds at which the tip assembly 102 and the distal portion 104 return to their non-deflected state based on moving the clutch control member 910. A circumference and/or outside surface of the clutch control member 910 can be textured, such as with grooves, to facilitate a user's ability to move it in a desired manner. While rotation of the clutch control member 910 is described, it is understood that any suitable type of actuation is contemplated, such as translation, movement along an arc, depression of a button, etc.

The clutch control member 910 includes a recess 912 that is sized and shaped in a corresponding manner to the clutch cam 920. The clutch cam 920 includes a threaded neck 922 and a shoulder 926. Posts 924 extend from the shoulder 926 in a direction opposite the neck 922. The posts 924 are received within bores 934 of the clutch spring 930. Axles 952, 954 extend through bores 932 of the clutch spring 930. The recess 912 of the clutch control member 910 is threaded in a corresponding manner as the threaded neck 922 of the clutch cam. When the handle 120 is assembled, clutch cam 920 is received within the recess 912. As the clutch control member 910 is rotated, the threads in the recess 912 engage the threaded neck 922.

Movement/rotation of the clutch control member 910 in the first direction (e.g., clockwise) causes the clutch cam 920 to move in the direction 1402, towards the clutch spring 930. That is, movement/rotation of the clutch control member 910 in the first direction (e.g., clockwise) applies a compression force on the clutch spring 930 via the clutch cam 920. The shoulder 926 applies the compression force upon contact with a central portion 936 of the clutch spring 930. Clutch spring 930 can be bent in its uncompressed state, as shown in FIG. 14. The central portion 936 of the clutch spring 930 straightens in response to the compression force from the clutch cam 920. An increase in the compression force causes in increase in the rotational resistance of the actuation control members 962, 964.

Movement/rotation of the clutch control member 910 in the second direction (e.g., counterclockwise) causes the clutch cam 920 to move in the direction 140, away the clutch spring 930. That is, movement/rotation of the clutch control member 910 in the second direction (e.g., counterclockwise) reduces or removes a compression force on the clutch spring 930 via the clutch cam 920. Clutch spring 930 returns to being bent, as in its uncompressed state, when the compression force is reduces or removed. The central portion 936 of the clutch spring 930 bends in response to the reduction/removal of compression force from the clutch cam 920. An increase in the compression force causes in increase in the rotational resistance of the actuation control members 962, 964.

Figure 15:
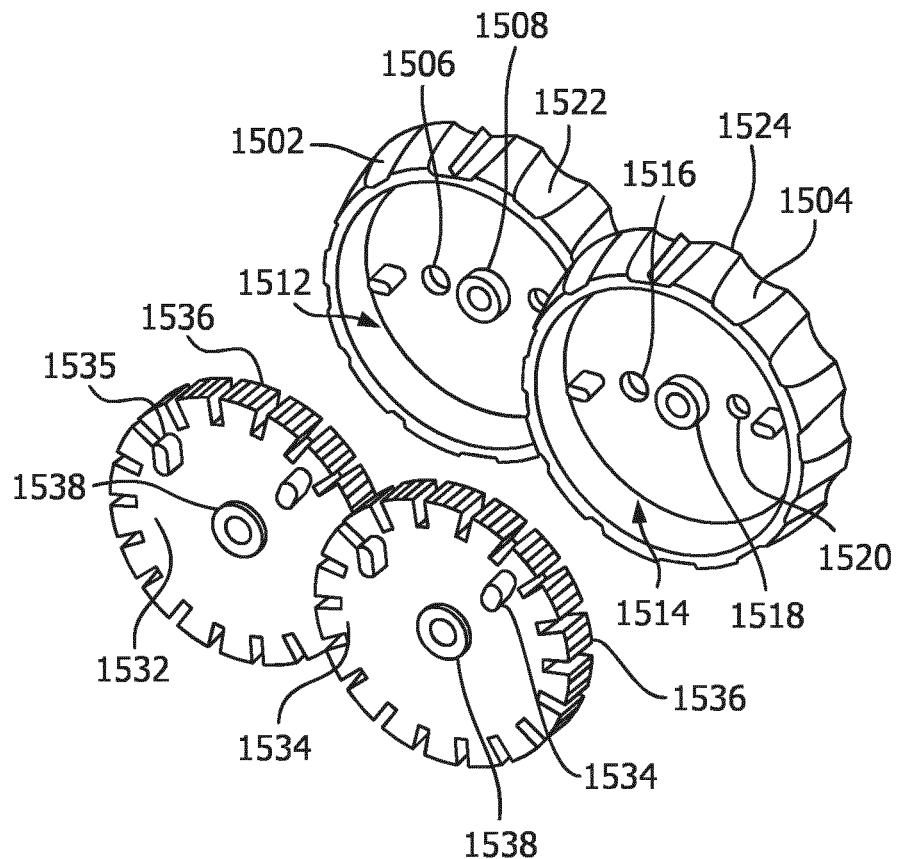
FIG. 15 is a diagrammatic perspective view of actuation control members and corresponding frictional members according to embodiments of the present disclosure.
Figure 16:
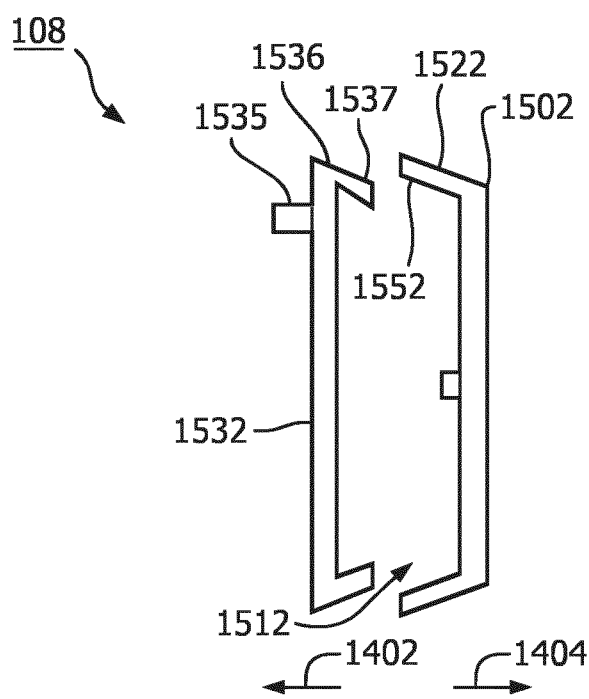
FIG. 16 is a diagrammatic side view of an actuation control member and a corresponding frictional member according to embodiments of the present disclosure.

FIG. 15 is a diagrammatic exploded perspective view of actuation control members 1502, 1504 and frictional members 1532, 1534. FIG. 16 is a diagrammatic exploded side view of the actuation control member 1502 and the frictional member 1532. The actuation control members 1502, 1504 can share similar features as the actuators 116 and the actuation control members 962, 964. An outer circumference 1522, 1524 of the actuation control members 962, 964 can be textured, such as with grooves, to facilitate movement, such as rotation, by the doctor's fingers. In some embodiments, linear markers can also be placed on the actuation control members 962, 964 to indicate a certain degree of device bending/steering or to indicate when the device is at a neutral straight position with no tensional forces acting upon it on any of the four directions. The actuation control members 962, 964 include bores 1508, 1518 through which the axles 952, 954 extend. The actuation control members 962, 964 also include bores or holes 1506, 1516, 1518 through which the posts 1032, 1036 of the pulleys 942, 944 extend. Cavities 1512, 1514 are formed on the side of the actuation control members 1502, 1504 adjacent to the frictional members 1532, 1534 and opposite the side on which the pulleys 942, 944 are disposed within the handle 120.

The frictional members 1532, 1534 can share similar features as the frictional members 972, 974. The frictional members 1532, 1534 include bores 1538 through which the axles 952, 954 extend. An outer circumference of the frictional members 1532, 1534 includes one or more interfering posts 1536. In some embodiments, the interfering posts 1536 extend completely around a circumference of the frictional members 1532, 1534. The interfering posts 1536 are oriented towards the cavities 1512, 1514 of the actuation control members 1502, 1504. The interfering posts 1536 can form a truncated cone shape for the frictional members 1532, 1534, in some examples. The cavities 1512, 1514 of the actuation control members 1502, 1504 form a chamber, including an inner circumferential surface 1552, that is shaped to mate with the interfering posts 1536 of the frictional members 1532, 1534. For example, as shown in the side view of FIG. 16, an exterior face 1537 of the interfering posts 1536 and the inner circumferential surface 1552 extend parallel to one another. When compression force is applied by the clutch cam 920 on the clutch spring 930, the actuation control members 1502, 1504 are moved in the direction 1402 towards the frictional members 1532, 1534. The inner circumferential surface 1552 of the actuation control members 1502, 1504 contacts the outer surface 1537 of the interfering posts 1536. Frictional contact between the interfering posts 1536 and the actuation control members 1502, 1504 hinders the movement, such as rotation, of the actuation control members 1502, 1504. That is, the rotational resistance of the actuation control members 1502, 1504 is increased. Thus, the actuation control members 1502, 1504 return to their quiescent state more slowly. In such circumstances, finer control of the deflection the tip assembly 102 and the distal portion 104 is achieved.

Less compression force causes the actuation control members 1502, 1504 to move in the direction 1404, away from the frictional members 1532, 1534. Less contact or no contact between the interfering posts 1536 and the actuation control members 1502, 1504 allows for the actuation control members 1502, 1504 to return to their quiescent state more quickly.

The frictional members 1532, 1534 and/or the interfering posts 1536 can be any suitable shape such that a surface of the frictional members 1532, 1532 contacts a corresponding surface of the control members 1502, 1504. In some embodiments, as shown in the cross-sectional image of FIG. 16, the frictional members 1532, 1534 have a truncated cone shape that is received within the correspondingly-shaped cavities 1512, 1514 of the control members 1502, 1504.

The frictional members 1532, 1534 include one or more locking posts 1535. The locking posts 1535 are positioned on a side of the frictional members 1532, 1534 opposite to the one or more interfering posts 1536. The locking post 1535 is configured to mechanically engage the alignment member 822 of the shells 810, 820. Engagement between the locking post 1535 and the alignment member 822 locks the rotation of the actuation control members 1502, 1504 such that the deflection of the tip assembly 102 and the distal portion 104 is maintained. In that regard, the physician can selectively cause the locking post 1535 to engage and to disengage the alignment member 822 based on movement of the actuation control members 1502, 1504.

Figure 17:
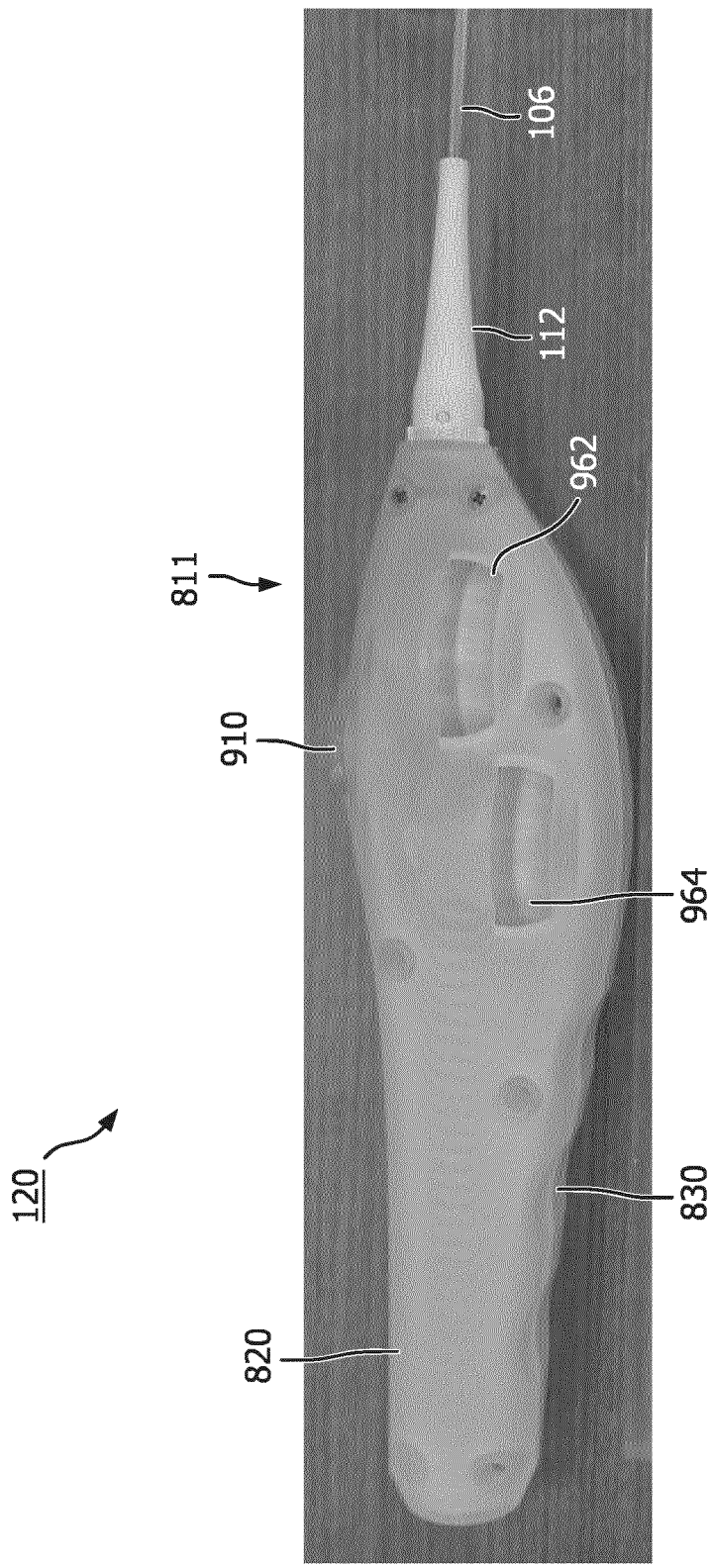
FIG. 17 is a perspective view of an assembled handle according to embodiments of the present disclosure.

FIG. 17 is a perspective view of the handle 120 in an assembled state. The handle 120 is configured such that a user can grasp the handle 120 and move the actuation control members 962, 964 and/or the clutch control member 910 using one or two hands. The actuation controls 962, 964 are positioned in line or parallel to a central longitudinal axis of the handle 120. In some embodiments, the actuation control 962 is aligned more closely with the central longitudinal axis while the actuation control 964 is transversely offset from longitudinal axis. For example, the actuation control associated with the more frequently used actuation direction can be aligned more closely with the central longitudinal axis. In one embodiment, the actuation control 962 controls deflection in the anterior-posterior direction. The illustrated embodiment shows distal strain relief 112 positioned around the tubular connection member 814. The bottom shell 820 is position around the junction of the distal strain relief 112 and the tubular connection member 814.

Figure 18:
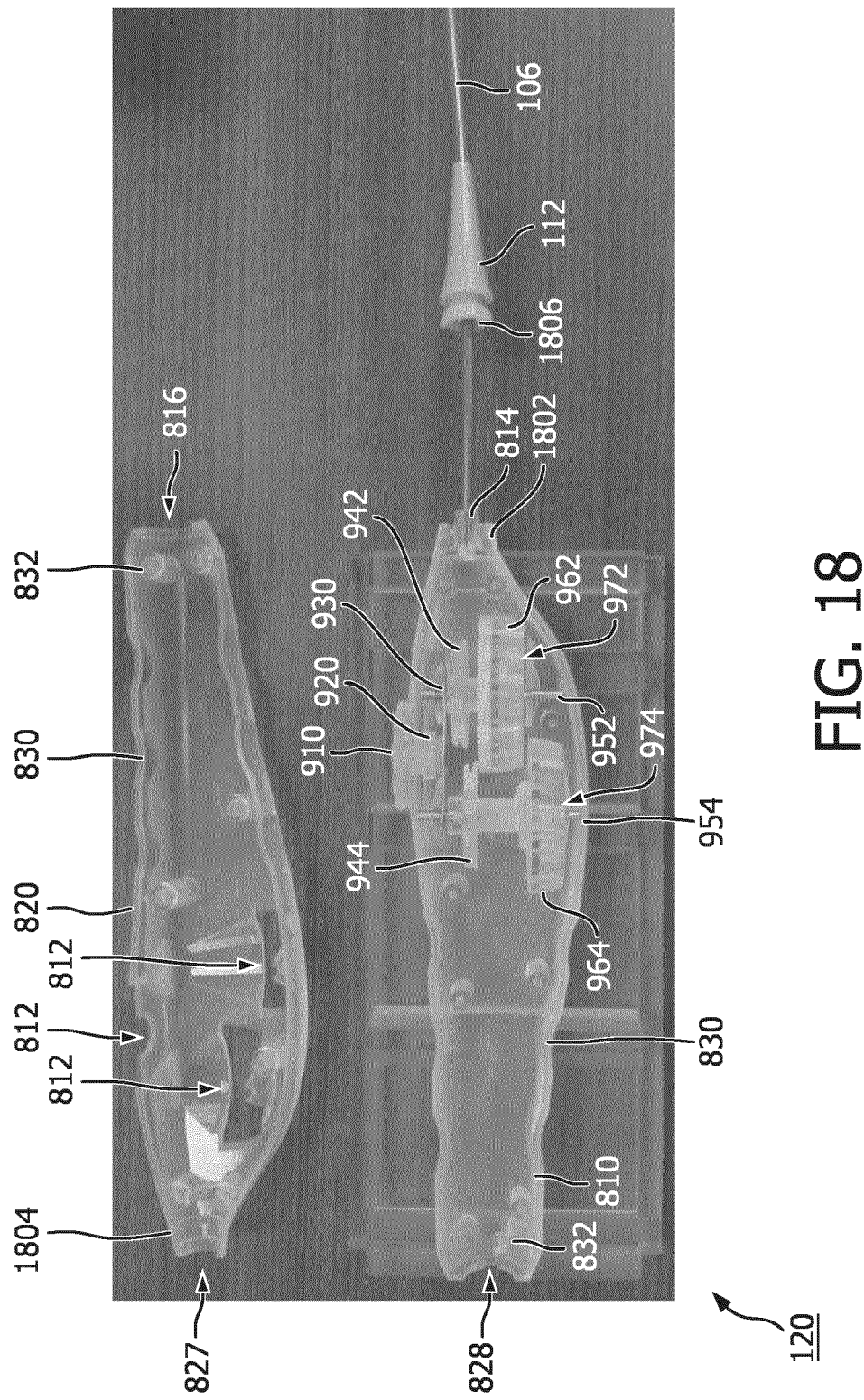
FIG. 18 is a perspective view of a partially assembled handle according to embodiments of the present disclosure.
Figure 19:
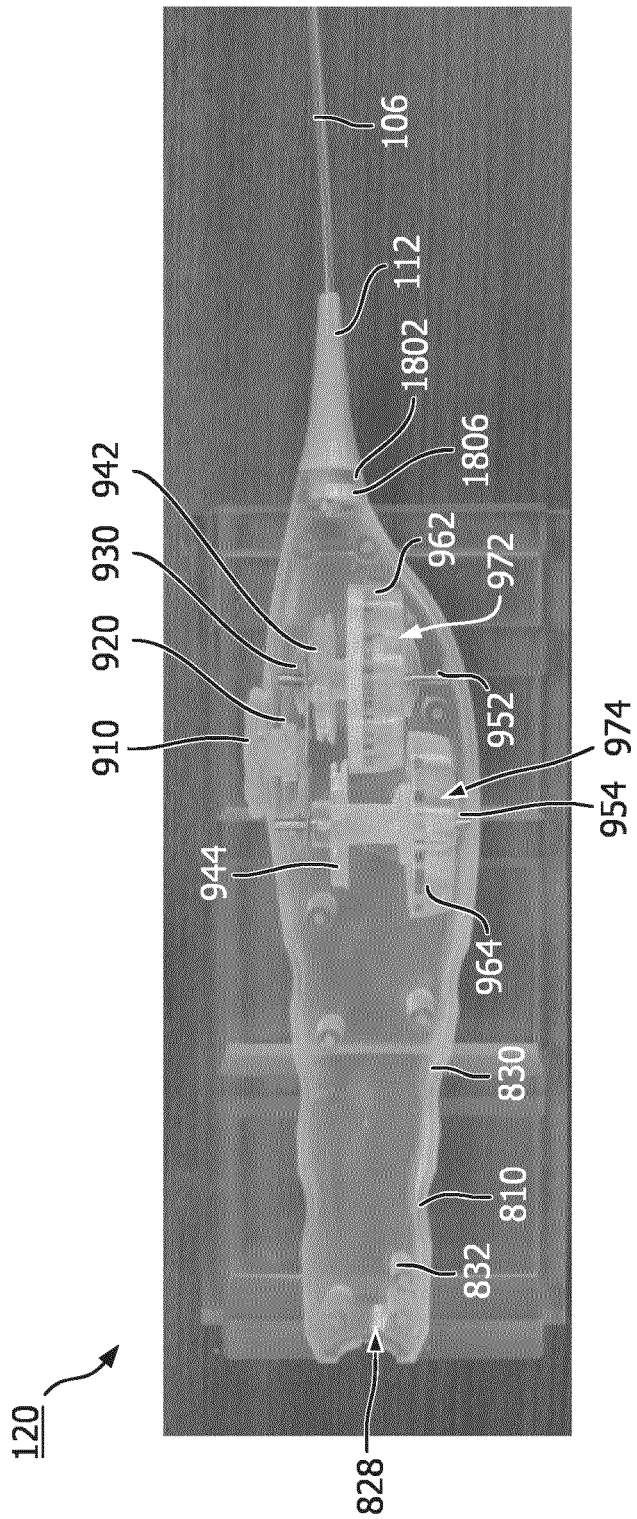
FIG. 19 is a perspective view of a partially assembled handle according to embodiments of the present disclosure.
Figure 20:
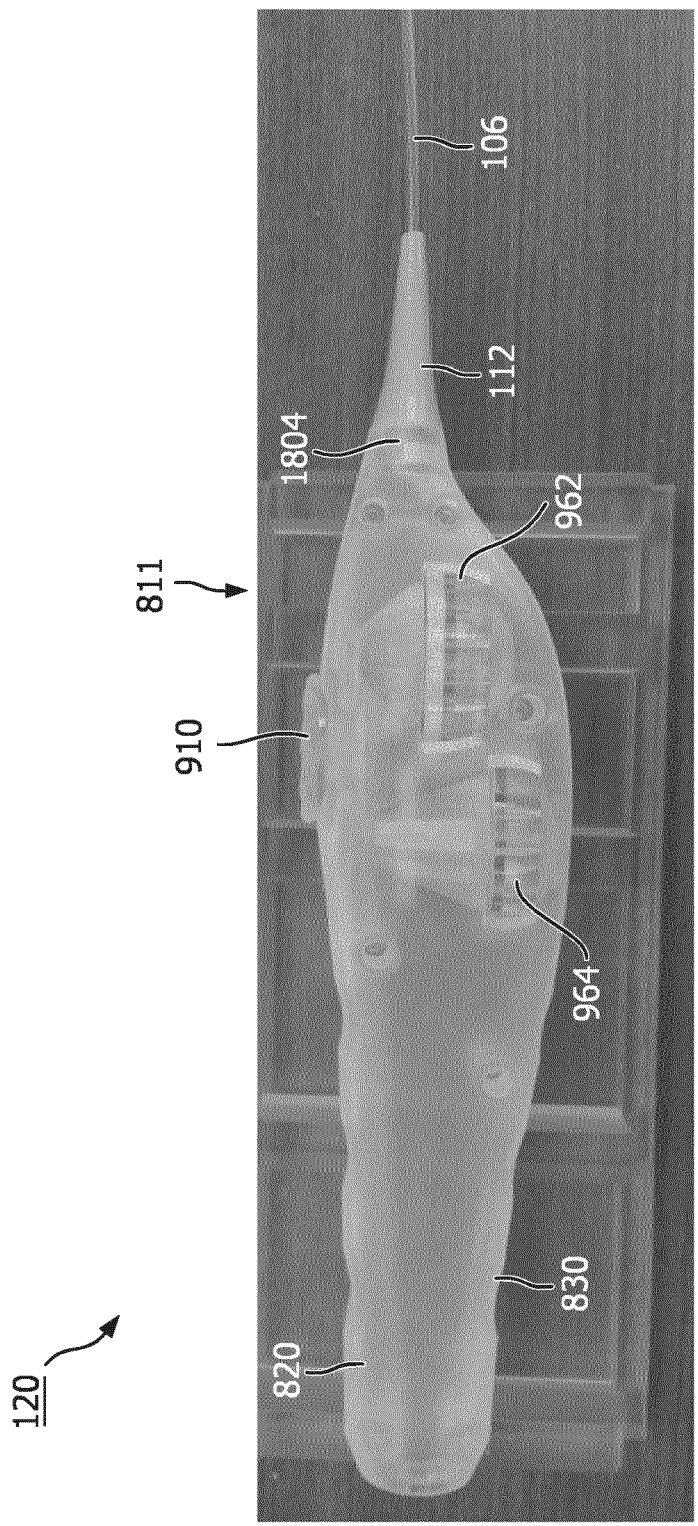
FIG. 20 is a perspective view of an assembled handle according to embodiments of the present disclosure.

FIGS. 18-20 illustrate an embodiment of the distal strain relief 112 having a locking feature 1806. FIGS. 18-20 are top views of the handle 120 over the course of method steps as the distal strain relief 112 is coupled to the handle 120. The proximal shaft has been attached to the upper shell 810 in FIG. 18. FIG. 18 additionally shows the distal strain relief 112 being passed proximally over shaft 106 towards the distal end 1802 of the top shell 810. The locking feature 1806 extends from the proximal portion of the strain relief 112. The distal end 1802 of the top shell 810 includes a corresponding space for the locking feature 1806. FIG. 19 illustrates the handle 120 once the strain relief 112 is coupled to the bottom shell 810. For example, the strain relief 112 can be pushed flush to the distal end 1802 of the shell 810. The strain relief 112 can be twisted to move the locking feature 1806 into a space within the distal end 1802, which mechanically locks the strain relief 112 to the shell 810. FIG. 20 shows the handle in an assembled state after the bottom shell 820 is positioned over the top shell 810. The handle 120 is configured such that a user can grasp the handle 120 and move the actuation control members 962, 964 and/or the clutch control member 910 using one or two hands.

The embodiment of FIGS. 18-20 creates an outer dome in the same surface alignment as the distal portion of the handle 120 around the proximal shaft slot on both the upper and lower shells 810, 820. The most distal diameter hole of this dome can slightly smaller than the diameter of the hole that adjacent and proximal. The adjacent, proximal hole can extend all the way up to the base of the proximal shaft slot. Additionally, a custom distal strain relief 112 can be used where there is a transition in the component from large outer diameter segment, smallest outer diameter segment, to another larger outer diameter segment on the vertical axis. The large diameter segment of the component, opposite of the tapered end of the strain relief 112, should be an offset diameter design where half of the segment's profile is a matching diameter to the smallest outer diameter segment on the component and the other half is the larger outer diameter to match the largest diameter in the dome feature of the shells 810, 820.

FIGS. 18 and 19 also show components of the steering control configuration 900 positioned within the handle 120. The clutch control member 910, the clutch cam 920, the clutch spring 930, the pulleys 942 and 944, the axles 952 and 954, the actuation control members 962 and 964, and the frictional members 972, 974 are positioned within the handle 120. The components of the configuration 900 can be positioned adjacent to or in contact with one another. As shown in FIGS. 18 and 19, the components of the configuration 900 can be directly or indirectly coupled to one another when the handle 120 is assembled. One or more components within the handle 120 can include edges specifically radiused to prevent wear and tear damages around the contact points of the pullwire segments.

Figure 21:
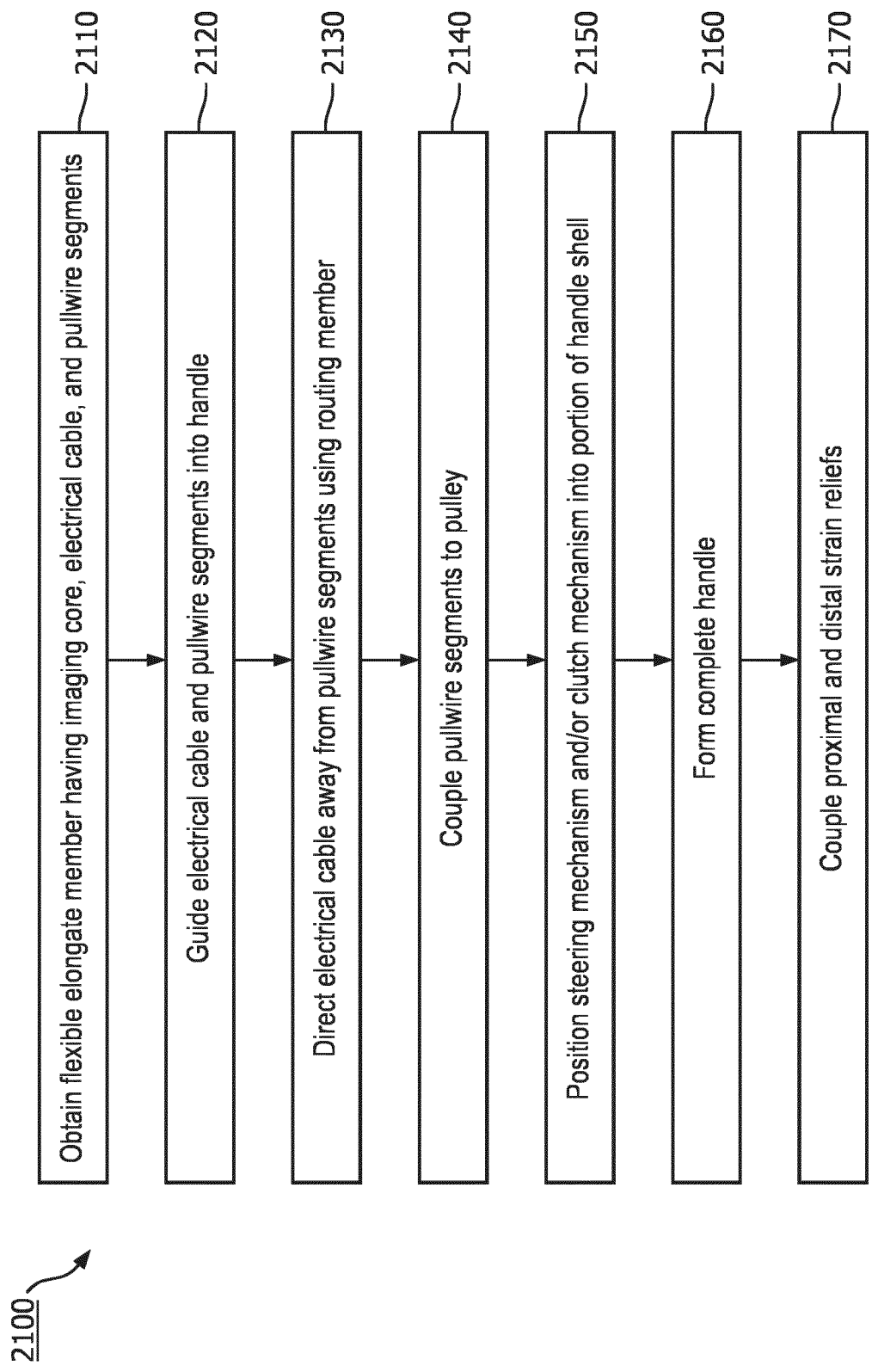
FIG. 21 is a flow diagram of a method of assembling an intraluminal imaging device according to embodiments of the present disclosure.

FIG. 21 is a flow diagram of a method 2100 of assembling an intraluminal imaging device, as described herein. It is understood that the steps of method 2100 may be performed in a different order than shown in FIG. 21, additional steps can be provided before, during, and after the steps, and/or some of the steps described can be replaced or eliminated in other embodiments. The steps of the method 2100 can be carried out by a manufacturer of the intraluminal imaging device.

At step 2110, the method 2100 includes obtaining a flexible elongate member. The flexible elongate member can include an imaging core at a distal portion. An electrical cable is in communication with the imaging core and extends along the length of the flexible elongate member from the distal portion to a proximal portion. One or more pullwires or pullwire segments that are configured to selectively deflect the distal portion of the flexible elongate member, including the image core, also extend along the length of the flexible elongate member from the distal portion to a proximal portion.

At step 2120, the method 2100 includes guiding the electrical cable and the pullwire segments into a handle of the intraluminal imaging device. For example, the electrical cable and the pullwire segments can enter through a lumen at a distal portion of the handle. In some embodiments, the handle includes a clam shell design made up for two or more components (e.g., a top shell and a bottom shell). Step 2120 can include guiding the electrical cable and the pullwire segments into the top shell or the bottom shell.

At step 2130, the method 2100 includes directing the electrical cable away from the pullwire segments using a routing member of the handle. For example, the routing member can divert the electrical such that the electrical cable is spaced from the pullwire segments.

At step 2140, the method 2100 includes coupling the pullwire segments to one or more pulleys. Each pulley can include a groove and one or more holes in communication with the groove. A first pullwire segment can be positioned along a first portion of the groove. A second pullwire segment can be positioned along a second portion of the groove. The first pullwire segment can extend from the groove through a first hole in the sidewall of the pulley. The second pullwire segment can extend from the groove through a second hole in the sidewall of the pulley. In some embodiments, both the first and second pullwire segments can extend through a third hole in the sidewall of the pulley. The first and second pullwire segments can coupled, such as by tying a knot, to an anchoring member.

At step 2150, the method 2100 includes positioning one or more components of a steering mechanism, including the one or more pulleys, and/or a clutch mechanism into the handle shell. For example, the one or more components of the steering mechanism can include a clutch control member, a clutch, a clutch spring, axles, actuation control members, and frictional members. The steering mechanism allows the distal portion of the flexible elongate member to be selectively deflected. The clutch mechanism allows the resistance of the actuation control members to be modified to control the rate at which the deflected distal portion returns to a non-deflected state.

At step 2160, the method 2100 includes forming a complete handle. For example, a second half of the handle shell can be positioned over and attached, such as by fixation members and/or adhesives, to the half of the handle shell containing the components of the steering mechanism (step 2150).

At step 2170, the method 2100 includes coupling proximal and distal strain reliefs to the handle. For example, the distal strain relief can be positioned over a shaft extending from the distal end of the handle. The proximal strain relief can be positioned over a cable extending from the proximal end of the handle.

Figure 22:
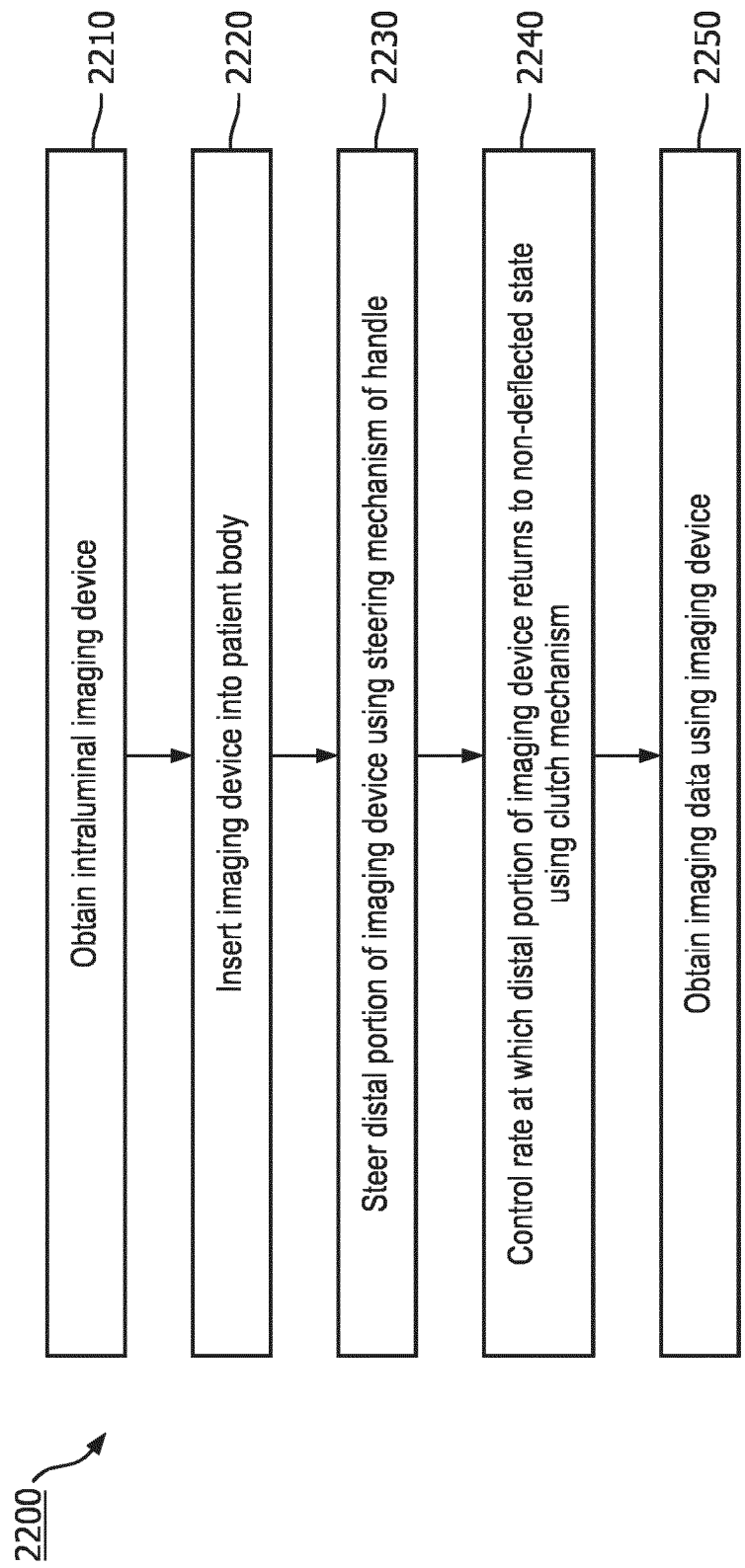
FIG. 22 is a flow diagram of a method of obtaining imaging data using an intraluminal imaging device according to embodiments of the present disclosure.

FIG. 22 is a flow diagram of a method 2200 of obtaining imaging data from within a patient body using an intraluminal imaging device. It is understood that the steps of method 2200 may be performed in a different order than shown in FIG. 22, additional steps can be provided before, during, and after the steps, and/or some of the steps described can be replaced or eliminated in other embodiments. The steps of the method 2200 can be carried out by a user of the intraluminal imaging device.

At step 2210, the method 2200 includes obtaining an intraluminal imaging device. The intraluminal imaging device can include flexible elongate member extending from a handle. A distal portion of the flexible elongate member can include an imaging core. The handle controls one or more pullwire segments extending along a length of the flexible elongate member to facilitate selective deflection of the distal portion, including the imaging core. At step 2220, the method 2200 includes inserting the imaging device into the patient body. For example, the imaging device can be positioned within any suitable lumen with the body.

At step 2230, the method 2200 includes steering the distal portion of the imaging using steering mechanism of handle. At step 2240, the method 2200 includes controlling the rate at which the distal portion of imaging device returns to non-deflected state using a clutch mechanism. One or more components of a steering mechanism can include pulley(s) coupled to the pullwire segment(s), axle(s), and actuation control member(s). The actuation control members can be coupled to the pullwire segments via the pulleys such that movement of the actuation control members causes corresponding deflection of the distal portion of the flexible elongate member. The clutch mechanism includes a clutch control member, a clutch cam, a clutch spring, and frictional members. The clutch control member can be moved to increase or decrease the compression force on the clutch cam. The clutch cam in turn applies the suitable compression force on the clutch spring. The frictional members are positioned adjacent to and/or in contact with the actuation control members. The actuation control members are urged into contact with the frictional members in response to the control force. Increased contact slows down the rate of return to the non-deflected state. Decreased contact speeds up the rate of return to the non-deflected state.

At step 2250, the method 200 includes obtaining imaging data using the imaging device from within the patient body. The method 2200 can further include any steps to review the obtained data.

Embodiments of the present disclosure provide numerous advantages. For example, the actuation directions of pullwires are in line with the actuation control members and pulleys for each respective direction, which reduces the force required to rotate the actuation control members and actuate the device. The present disclosure provides a device with the ability to actuate to angle significantly higher than the commercial devices on the market with less force, and in a more direct responsive action via the actuation control members (less rotation, less control dead zones, etc.). Use of a lined variable braided differential durometer multi-lumen shaft increase this efficiency.

Additionally, the wire pathway between the proximal shaft to the pulleys are designed so each pull wire is adequately separated from one another so putting tension on a single wire will not unintentionally put tension on another and be subjected to wire to wire abrasion. The present disclosure also limits the amount of angles subjected to the pullwires as it travels from the shaft to the pulleys for a more direct and efficient application of the force exerted by rotating the actuation control members. This enables a high stroke of actuation with a slight rotation of the actuation control members, increasing the usability of the device overall by allowing embodiments described herein to be adapted to a wide range of sensitivity when optimizing device usability.

The overall ergonomic shape of the embodiments described herein and the ability to place both fingers on the desired actuation control members when rotating to control actuation is intended to provide the physician the ability to use the handle from any rotational angle while granting grip stability and conserving tactile resolution as much as possible. The shape, the finger grooves on the proximal end, the proximity and offset positioning of the actuation control members, as well as the different size and shapes of each actuation control member and the brake controls from one another was intended to allow the physicians to use the device one handed, with either hands, and to allow them to intuitively control the handle without directly looking at it.

The variable braking system allows the user to select the proper balance between the feedback resistance felt on the actuation control members during steering and the holding force they desire on the actuation control members to keep their current actuated state upon their release of the actuation control members. The frictional members used as the base of the actuation control members and functioning as part of the variable braking system also works together with the outer housing. The actuation control members themselves to create interfering posts to limit the device's actuation range. Actuation range and wheel rotation can also be limited independent of one another. Stroke to wheel rotation ratio can now be further optimized for usability by simply altering the interfering posts on these components and the size of the pulley themselves without having to make any modifications to the shaft of the device itself.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
   a flexible elongate shaft including a distal portion and a proximal portion, wherein the flexible elongate shaft is configured for insertion into a patient body;
   a distal tip that comprises an imaging element and is operably associated with the distal portion of the flexible elongate shaft; and
   a control handle coupled to the proximal portion of the flexible elongate shaft,
   wherein the control handle includes:
      a first actuator configured to position the imaging element within the patient body; and
      a first frictional member coupled to the first actuator and arranged to contact the first actuator to control positioning of the imaging element,
   wherein the first actuator includes:
      a first pulley member coupled to a first pair of pullwire segments, wherein the first pair of pullwire segments are coupled to the distal portion of the flexible elongate shaft; and
      a first actuation control member coupled to the first pulley member and configured to apply tension to the first pair of pullwire segments such that the imaging element and the distal portion of the flexible elongate shaft are deflected along a first plane,
   wherein the first pulley member includes a plurality of holes radially spaced apart on a side of the first pulley member,
   wherein the first pair of pullwire segments are threaded through the plurality of holes.

2. The intraluminal imaging device of claim 1, wherein the first frictional member is positioned on a side of the first actuation control member opposite to the first pulley member.

3. The intraluminal imaging device of claim 1, wherein:
   an outer circumference of the first frictional member includes one or more interfering posts oriented towards a cavity of the first actuation control member;
   the one or more interfering posts contact the first actuation control member in response to application of a compression force on the first actuation control member; and
   contact between the interfering posts and the first actuation control member changes rotational resistance of the first actuation control member.

4. The intraluminal imaging device of claim 3, wherein the control handle further includes:
   a clutch spring coupled to the first pulley member;
   a clutch cam coupled to the clutch spring; and a clutch control member coupled to the clutch cam such that adjustment of the clutch control member causes the clutch cam to compress the clutch spring towards the first pulley member such that the compression force is applied to the first actuation control member.

5. The intraluminal imaging device of claim 4, wherein the control handle further includes a housing having an elongate shape, wherein the first frictional member, the first actuator, the clutch spring, the clutch cam, and the clutch control member are disposed at a distal portion of the housing, and wherein the housing includes a plurality of finger-shaped grooves positioned on an outer surface of a proximal portion of the housing.

6. The intraluminal imaging device of claim 5, wherein the control handle further includes:
an axle extending through the clutch spring, the first pulley member, the first actuation control member, and the first frictional member,
wherein the housing includes a plurality of alignment members arranged to receive the axle.

7. The intraluminal imaging device of claim 6, wherein the first frictional member further includes a locking post positioned on a side of the first frictional member opposite to the one or more interfering posts, and wherein the first actuation control member is maintained at a current position when the locking post is locked to one of the plurality of alignment members.

8. The intraluminal imaging device of claim 1, wherein the first actuation control member includes a first slot and a second slot, wherein the first pulley member includes a first post received within the first slot and a second post received within the second slot, and wherein the first post and the second post have different diameters.

9. The intraluminal imaging device of claim 8, wherein the side of the first pulley member is opposite to the first post and the second post.

10. The intraluminal imaging device of claim 1,
wherein the first pulley member includes:
an anchoring member disposed on an edge of the first pulley member,
wherein the first pair of pullwire segments are secured to the anchoring member.

11. The intraluminal imaging device of claim 1, wherein the control handle further comprises:
a second actuator including:
a second pulley member coupled to a second pair of pullwire segments, wherein the second pair of pullwire segments are coupled to the distal portion of the flexible elongate shaft; and
a second actuation control member coupled to the second pulley member and configured to apply tension to the second pair of pullwire segments such that the imaging element and the distal portion of the flexible elongate shaft are deflected along a second plane different from the first plane; and
a second frictional member coupled to the second actuator and arranged to contact the second actuator to control positioning of the imaging element.

12. The intraluminal imaging device of claim 11, further comprising:
a housing having an elongate shape, wherein the first actuation control member and the second actuation control member are positioned lengthwise along the housing.

13. The intraluminal imaging device of claim 12, wherein the housing includes a routing member configured to orient a coaxial cable coupled to the imaging element such that the coaxial cable is spaced from the first pair of pullwire segments and the second pair of pullwire segments within the housing.

14. The intraluminal imaging device of claim 11, wherein the first actuator is aligned with a central longitudinal axis of the flexible elongate shaft, and wherein the second actuator is offset from the central longitudinal axis such that actuations of the first pair of pullwire segments and the second pair of pullwire segments are independent of each other.

15. The intraluminal imaging device of claim 11, wherein the first plane is a left-right articulation plane, wherein the second plane is an anterior-posterior articulation plane, and wherein the first actuation control member is larger in size than the second actuation control member.

16. An intraluminal imaging device, comprising:
a flexible elongate shaft including a distal portion and a proximal portion, wherein the flexible elongate shaft is configured for insertion into a patient body;
a distal tip that comprises an imaging element and is operably associated with the distal portion of the flexible elongate shaft; and
a control handle coupled to the proximal portion of the flexible elongate shaft,
wherein the control handle includes:
a first actuator configured to position the imaging element within the patient body; and
a first frictional member coupled to the first actuator and arranged to contact the first actuator to control positioning of the imaging element,
wherein the first actuator includes:
a first pulley member coupled to a first pair of pullwire segments, wherein the first pair of pullwire segments are coupled to the distal portion of the flexible elongate shaft; and
a first actuation control member coupled to the first pulley member and configured to apply tension to the first pair of pullwire segments such that the imaging element and the distal portion of the flexible elongate shaft are deflected along a first plane,
wherein the first pulley member includes an anchoring member disposed on an edge of the first pulley member,
wherein the first pair of pullwire segments are secured to the anchoring member.

17. The intraluminal imaging device of claim 16, wherein the first frictional member is positioned on a side of the first actuation control member opposite to the first pulley member.

18. The intraluminal imaging device of claim 16, wherein:
an outer circumference of the first frictional member includes one or more interfering posts oriented towards a cavity of the first actuation control member;
the one or more interfering posts contact the first actuation control member in response to application of a compression force on the first actuation control member; and
contact between the interfering posts and the first actuation control member changes rotational resistance of the first actuation control member.

19. The intraluminal imaging device of claim 18, wherein the control handle further includes:
a clutch spring coupled to the first pulley member;
a clutch cam coupled to the clutch spring; and
a clutch control member coupled to the clutch cam such that adjustment of the clutch control member causes the clutch cam to compress the clutch spring towards the first pulley member such that the compression force is applied to the first actuation control member.

20. The intraluminal imaging device of claim 19, wherein the control handle further includes a housing having an elongate shape, wherein the first frictional member, the first actuator, the clutch spring, the clutch cam, and the clutch control member are disposed at a distal portion of the housing, and wherein the housing includes a plurality of finger-shaped grooves positioned on an outer surface of a proximal portion of the housing.

21. The intraluminal imaging device of claim 20, wherein the control handle further includes:
an axle extending through the clutch spring, the first pulley member, the first actuation control member, and the first frictional member,
wherein the housing includes a plurality of alignment members arranged to receive the axle.

22. The intraluminal imaging device of claim 21, wherein the first frictional member further includes a locking post positioned on a side of the first frictional member opposite to the one or more interfering posts, and wherein the first actuation control member is maintained at a current position when the locking post is locked to one of the plurality of alignment members.

23. The intraluminal imaging device of claim 16,
wherein the first pulley member includes a plurality of holes radially spaced apart on a side of the first pulley member,
wherein the first pair of pullwire segments are threaded through the plurality of holes.

24. The intraluminal imaging device of claim 23, wherein the first actuation control member includes a first slot and a second slot, wherein the first pulley member includes a first post received within the first slot and a second post received within the second slot, and wherein the first post and the second post have different diameters.

25. The intraluminal imaging device of claim 24, wherein the side of the first pulley member is opposite to the first post and the second post.

26. The intraluminal imaging device of claim 16, wherein the control handle further comprises:
a second actuator including:
a second pulley member coupled to a second pair of pullwire segments, wherein the second pair of pullwire segments are coupled to the distal portion of the flexible elongate shaft; and
a second actuation control member coupled to the second pulley member and configured to apply tension to the second pair of pullwire segments such that the imaging element and the distal portion of the flexible elongate shaft are deflected along a second plane different from the first plane; and
a second frictional member coupled to the second actuator and arranged to contact the second actuator to control positioning of the imaging element.

27. The intraluminal imaging device of claim 26, further comprising:
a housing having an elongate shape, wherein the first actuation control member and the second actuation control member are positioned lengthwise along the housing.

28. The intraluminal imaging device of claim 27, wherein the housing includes a routing member configured to orient a coaxial cable coupled to the imaging element such that the coaxial cable is spaced from the first pair of pullwire segments and the second pair of pullwire segments within the housing.

29. The intraluminal imaging device of claim 26, wherein the first actuator is aligned with a central longitudinal axis of the flexible elongate shaft, and wherein the second actuator is offset from the central longitudinal axis such that actuations of the first pair of pullwire segments and the second pair of pullwire segments are independent of each other.

30. The intraluminal imaging device of claim 26, wherein the first plane is a left-right articulation plane, wherein the second plane is an anterior-posterior articulation plane, and wherein the first actuation control member is larger in size than the second actuation control member.

* * * * *